US011266355B2

(12) United States Patent
Roberts et al.

(10) Patent No.: US 11,266,355 B2
(45) Date of Patent: Mar. 8, 2022

(54) EARLY WARNING SYSTEM AND METHOD FOR PREDICTING PATIENT DETERIORATION

(71) Applicant: CERNER INNOVATION, INC., Kansas City, KS (US)

(72) Inventors: Andrew Roberts, Overland Park, KS (US); Sasanka Are, Kansas City, MO (US); Douglas S. McNair, Leawood, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 97 days.

(21) Appl. No.: 15/983,348

(22) Filed: May 18, 2018

(65) Prior Publication Data

US 2018/0333106 A1  Nov. 22, 2018

Related U.S. Application Data

(60) Provisional application No. 62/508,808, filed on May 19, 2017.

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0022* (2013.01); *A61B 5/0205* (2013.01);
(Continued)

(58) Field of Classification Search
CPC ... A61B 5/0022; A61B 5/0205; A61B 5/4842; G16H 40/20; G16H 10/60; G16H 50/30; G16H 50/20
(Continued)

(56) References Cited

U.S. PATENT DOCUMENTS 7,196,590 B1 * 3/2007 In ........................... H03B 21/01
  331/2
10,877,074 B1 * 12/2020 Bulsara .............. G01R 33/0041
(Continued)

OTHER PUBLICATIONS

"Sollers et al., Comparison of the Ratio of the Standard Deviation of the R-R Interval and the Root Mean Squared Successive Differences (SD/rMSSD) to the Low Frequency-to-High Frequency (LF/HF) Ratio in a Patient Population and Normal Healthy, 2007, Biomedical Science Instrumentation, 43, 158-163" (Year: 2007).*
(Continued)

*Primary Examiner* — Carl H Layno
*Assistant Examiner* — Manolis Pahakis
(74) *Attorney, Agent, or Firm* — Shook Hardy & Bacon L.L.P.

(57) ABSTRACT

Methods and systems for predicting deterioration of a patient's condition within a future time interval based on a time series of values for monitored physiological variables measured from a patient, and in some instances, providing advanced notice to clinicians or caregivers when deterioration is forecasted or modifying treatment for the patient are provided. In particular, deterioration of a patient's condition is based on a Hopf bifurcation model and is predicted using a ratio of deviations for monitored physiological variables. A ratio of deviations relates the standard deviation and root mean square of successive differences for a set of physiological values measured over time. The RoD for one or more variables, such as heart rate, respiratory rate, and blood pressure, may be used to predict the likelihood of the patient's condition deteriorating into an unstable state as what occurs in a Hopf bifurcation.

20 Claims, 21 Drawing Sheets

(51) Int. Cl.
| G16H 50/20 | (2018.01) |
| G16H 40/20 | (2018.01) |
| G16H 10/60 | (2018.01) |
| G16H 50/30 | (2018.01) |
| A61B 5/021 | (2006.01) |
| A61B 5/024 | (2006.01) |
| A61B 5/08 | (2006.01) |

(52) U.S. Cl.
CPC ........... *A61B 5/4842* (2013.01); *G16H 10/60* (2018.01); *G16H 40/20* (2018.01); *G16H 50/20* (2018.01); *G16H 50/30* (2018.01); *A61B 5/021* (2013.01); *A61B 5/024* (2013.01); *A61B 5/0816* (2013.01); *A61B 2503/06* (2013.01)

(58) Field of Classification Search
USPC .......................................................... 600/301
See application file for complete search history.

(56) References Cited

U.S. PATENT DOCUMENTS

| 2003/0154225 | A1* | 8/2003 | Neubert | G06F 17/10 |
| | | | | 708/446 |
| 2007/0249948 | A1* | 10/2007 | Gilmour | A61B 5/361 |
| | | | | 600/518 |
| 2008/0306564 | A1* | 12/2008 | Wei | A61B 5/283 |
| | | | | 607/18 |
| 2009/0292180 | A1* | 11/2009 | Mirow | G16H 10/20 |
| | | | | 600/301 |
| 2010/0234748 | A1* | 9/2010 | Moorman | G16H 10/20 |
| | | | | 600/509 |
| 2011/0172504 | A1* | 7/2011 | Wegerich | A61B 5/0205 |
| | | | | 600/301 |
| 2011/0224565 | A1* | 9/2011 | Ong | A61B 5/04014 |
| | | | | 600/509 |
| 2015/0302165 | A1* | 10/2015 | Aihara | G16H 10/40 |
| | | | | 702/19 |
| 2018/0333106 | A1* | 11/2018 | Roberts | G16H 50/30 |
| 2019/0223779 | A1* | 7/2019 | Mersmann | G16H 50/50 |
| 2019/0254585 | A1* | 8/2019 | Jirsa | A61B 5/4094 |
| 2021/0268289 | A1* | 9/2021 | Tass | A61N 1/0534 |

OTHER PUBLICATIONS

Baer et al., "The Slow Passage through a Hopf Bifurcation: Delay, Memory Effects, and Resonance", SIAM Journal on Applied Mathematics, vol. 49, No. 1, Feb. 1989, pp. 55-71.

Boettiger et al., "Early Warning Signals: The Charted and Uncharted Territories", Theoretical Ecology, vol. 6, No. 3, May 30, 2013, pp. 1-12.

Chen et al., "Detecting Early-warning Signals for Sudden Deterioration of Complex Diseases by Dynamical Network Biomarkers", Scientific Reports, vol. 2, Article No. 342, Mar. 29, 2012, pp. 1-8.

Dakos et al., "Methods for Detecting Early Warnings of Critical Transitions in Time Series Illustrated Using Simulated Ecological Data", PloS One, vol. 7, Issue 7, e41010, Jul. 2012, pp. 1-20.

Dakos et al., "Slowing Down as an Early Warning Signal for Abrupt Climate Change", Proceedings of the National Academy of Sciences, vol. 105, No. 38, Sep. 23, 2008, pp. 14308-14312.

Ditlevsen et al., "Tipping Points: Early Warning and Wishful Thinking", Geophysical Research Letters, vol. 37, No. 19, Oct. 2, 2010, pp. 1-4.

Glendinning, Paul, "Stability, Instability and Chaos: An Introduction to the Theory of Nonlinear Differential Equations", Chapters 7 and Chapter 8.8-8.10, Cambridge University Press, vol. 11, 1994.

Kéfi et al., "Early Warning Signals Also Precede Non-Catastrophic Transitions", Oikos, vol. 122, No. 5, 2013, pp. 641-648.

Krupa et al., "Relaxation Oscillation and Canard Explosion", Journal of Differential Equation, vol. 174, No. 2, 2001, pp. 312-368.

Lenton, Timothy M., "Early Warning of Climate Tipping Points", Nature Climate Change, vol. 1, No. 4, Jul. 2011, pp. 201-209.

Strogatz, Steven H., "Nonlinear Dynamics and Chaos: With Applications to Physics, Biology, Chemistry, and Engineering", Chapters 7.1, 7.6, and 8.2, Westview press, 2014.

Van de Leemput et al., "Critical Slowing Down as Early Warning for the Onset and Termination of Depression", Proceedings of the National Academy of Sciences, vol. 111, No. 1, Jan. 7, 2014, pp. 87-92.

Wechselberger, Martin, "Canards", Scholarpedia, vol. 2, No. 4, 1356, Available online at: <http://www.scholarpedia.org/article/Canards>, 2007, pp. 1-7.

* cited by examiner

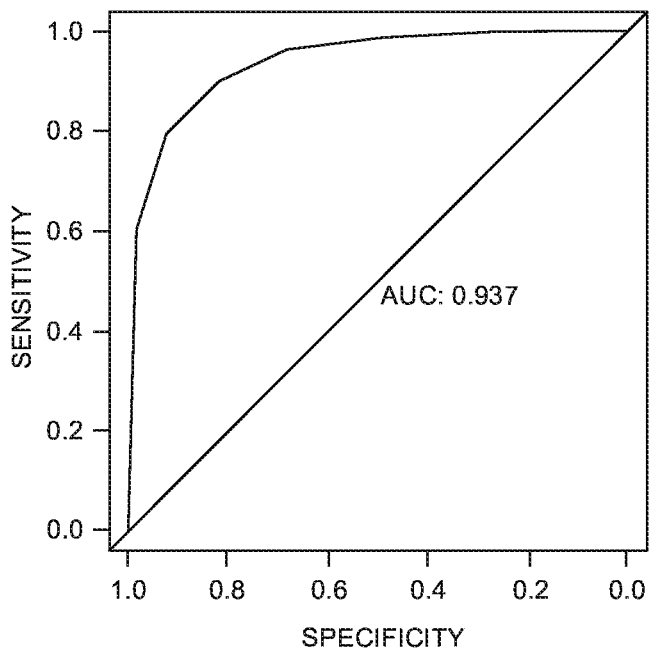
(a) $a = 10$ (NORMAL)
*FIG. 9A.*
*FIG. 9B.*
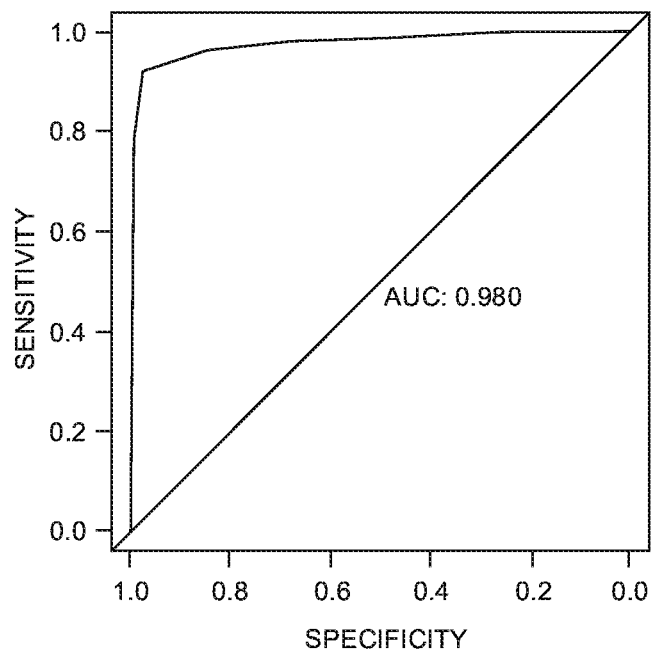
(b) $a = 10$ (EXCITABLE)

```
###############################################################

# Example RoD For Early Warning Signal

###############################################################

# Function to detect a change in a 3D system
detect.3d <- function(traj,score = 'rod', lkbk = NULL){
  # traj = 3D trajectory stored as list, with variables named 'x', 'y', 'z', and 'tt' (time)

# choose scoring method:
  #   rod       => positive if RoD increases
  #   rod.var   => positive if both RoD and SD (or variancE) increase
  #   rod.rmssd => positive if both RoD and RMSSD increse x <- as.numeric( unlist( traj$x ) )
  y <- as.numeric( unlist( traj$y ) )
  z <- as.numeric( unlist( traj$z ) )

tt <- as.numeric( unlist( traj$tt ) )

rod.x <- compRod(x, tt, lookback=lkbk )  # returns vector of 0s (no change detected), and 1s (change detected)
  rod.y <- compRod(y, tt, lookback=lkbk )
  rod.z <- compRod(z, tt, lookback=lkbk )
  rods <- list(rod       = rod.x$score       + rod.y$score       + rod.z$score,
               rod.var   = rod.x$score.var   + rod.y$score.var   + rod.z$score.var,
               rod.rmssd = rod.x$score.rmssd + rod.y$score.rmssd + rod.z$score.rmssd)

positive <- sum(rods[[score]]==3) > 0  # Boolean variable, True if there is a time when all coordinates x,y,z register a change return(positive)
}

Calls these functions-----
compRod <- function( x, tt, st.ind=4, lookback=NULL ){
  # x = vector (time series) of observations
  # tt = times of observations
  # st.ind = min.number of observations before you can register a positive
  # lookback = limit observations to most recent len <- length(x)

if(!is.null(lookback)){
    c1 <- unlist( lapply ( st.ind:len, function(j) rmssd(  x, ind=j, t=tt, lkbk=lookback ) ) )
    c2 <- unlist( lapply ( st.ind:len, function(j) sd.lkbk( x, ind=j, t=tt, lkbk=lookback ) ) )
  }else{
    c1 <- unlist( lapply ( st.ind:len, function(j) rmssd(  x, ind=j, t=tt, lkbk=NULL ) ) )
    c2 <- unlist( lapply ( st.ind:len, function(j) sd.lkbk( x, ind=j, t=tt, lkbk=NULL ) ) )
  }
```

FIG. 10A.

Continues in FIG. 10B

Continues FROM FIG. 10A

```
c1 <- c(rep(0,st.ind-1),c1)
c2 <- c(rep(0,st.ind-1),c2)
pos.inds2 <- which(c2 > 0)

c3 <- rep(0,len)
c3[pos.inds2] <- c1[pos.inds2]/c2[pos.inds2]
pos.inds3 <- which(c3 > 0)
pos.inds3.1 <- pos.inds3 + 1 c4 <- rep(0,len)
c4[pos.inds3.1] <- floor(c3[pos.inds3.1]/c3[pos.inds3])
c4 <- c4[1:len]
c4.1 <- unlist(lapply(c4,function(x) min(x,1) ) )

c5 <- c4.1
c6 <- c4.1 c1.1 <- c1[1:(len-1)]
c1.2 <- c1[2:len]
inds.rmssd <- which(c1.2 < c1.1)

c2.1 <- c2[1:(len-1)]
c2.2 <- c2[2:len]
inds.var <- which(c2.2 < c2.1)

if(length(inds.var) > 0) c5[inds.var+1] <- 0      # require both RoD and SD to increase
if(length(inds.rmssd) > 0) c6[inds.rmssd+1] <- 0     # require both RoD and RMSSD to increase y <- list(rmssd = c1, sd = c2, rod = c3, score = c4.1, score.var = c5, score.rmssd = c6)
return(y)

}
```

Continues IN FIG. 10C

*FIG. 10B*

Continues FROM FIG. 10B

```
rmssd <- function(x,ind,t=NULL,lkbk = NULL){ if(!is.null(lkbk)){
    min.ind <- min(which(t >= t[ind]-lkbk)) # will send error if lkbk != NULL but no 't' specified
  } else{
    min.ind <- 1
  } x <- x[min.ind:ind]

n.obs <- length(x)

if(n.obs > 1){
    ssds <- unlist( lapply(2:n.obs, function(j) (x[j]-x[j-1])^2 ) )
    ssd <- sum(ssds)
    y <- sqrt(ssd/(n.obs-1))
  } else{y=0} return(y)
} sd.lkbk <- function(x,ind,t=NULL,lkbk = NULL ){
  if(!is.null(lkbk)){
    min.ind <- min(which(t >= t[ind]-lkbk)) # will send error if lkbk != NULL but no 't' specified
  } else{
    min.ind <- 1
  } x <- x[min.ind:ind]

return(sd(x))
}
```

FIG. 10C

EARLY WARNING SYSTEM AND METHOD FOR PREDICTING PATIENT DETERIORATION

CROSS-REFERENCE TO RELATED APPLICATIONS

This application claims the benefit of U.S. Provisional Application No. 62/508,808 titled "EARLY WARNING SYSTEM AND METHOD FOR PREDICTING PATIENT DETERIORATION," filed on May 19, 2017, which is hereby expressly incorporated by reference in its entirety.

BACKGROUND

Early intervention and stabilization of a patient's deteriorating clinical condition is often critical, especially for certain populations of patients susceptible to sudden changes in a condition. For example, clinical deterioration in pediatric patients often occurs rapidly. Accordingly, clinicians proactively monitor pediatric patients for early warning signs of deterioration. One current practice for such monitoring is having nurses use the Pediatric Early Warning System (PEWS) to monitor and score pediatric patients' conditions based on visual observations of the patient. However, the current PEWS scoring methods introduce some variance based on the observing nurse, the nurse's experience, the hospital unit, or the patient's underlying condition, all of which affects the accuracy of the PEWS score. Additionally, these current methods utilize visual observations by a caregiver, which can only be done periodically, and the time in which the current systems often detects a future critical event in the patient's condition is sometimes insufficient to provide effective intervention.

SUMMARY

Systems, methods and computer-storage media are provided for a decision support tool for predicting deterioration of a patient based on a time series of monitored physiological variables measured from a patient and, in some instances, for providing advanced notice to clinicians and caregivers when such deterioration is forecasted or modifying treatment for the patient according to the predicted likelihood. In particular, an early warning decision support system is provided for determining a likelihood of significant or meaningful deterioration in patient conditions, such as the condition of pediatric patients. Embodiments of the disclosure described herein may provide a forecasted risk for future deterioration within a time horizon comprising a future time interval. In one embodiment, the future time interval is from approximately thirty minutes to twenty hours into the future and may be dependent on the frequency of the physiological measurements and/or the particular patient condition.

Aspects described herein include a decision support tool that forecasts deterioration of a patient's condition based on a bifurcation model, such as a Hopf bifurcation model. Bifurcation in a patient's system can be detected before the patient's condition becomes noticeably unstable, and measurements may be taken to prevent or mitigate the effects of significant instability. Deterioration occurring in a future time interval may be determined by monitoring certain physiological variables for the patient, such as heart rate, respiratory rate, and mean arterial pressure, and using these physiological measurements may generate an indication or likelihood of future deterioration by the patient. In particular, the likelihood of future deterioration is based on a ratio of deviation determined for the physiological variables and may be determined based on a standard deviation and a root mean square of successive differences using the patient's monitored physiological measurements. Based on the determined ratios of deviations for the patient, a likelihood of the patient's condition deteriorating within a future time interval is determined, and a response may be initiated to provide preventative or therapeutic interventions. Accordingly, one aim of embodiments of this disclosure is to improve upon conventional industry practice by deriving accurate predictive capabilities to provide more effective treatment and care.

BRIEF DESCRIPTION OF THE DRAWINGS

The present invention is described in detail below with reference to the attached drawing figures, wherein:

FIGS. 9A-9B depict Receiver Operating Characteristic (ROC) curves representing accuracy and discriminating classificatory capability and the statistical performance of embodiments reduced to practice for a normal system and an excitable system; and FIGS. 10A-10C depict an example embodiment of a computer program routine using ratio of deviations as an early warning signal for predicting deterioration of a patient's condition within a future time interval, in accordance with an embodiment of the disclosure.

DETAILED DESCRIPTION

Figure 1A:
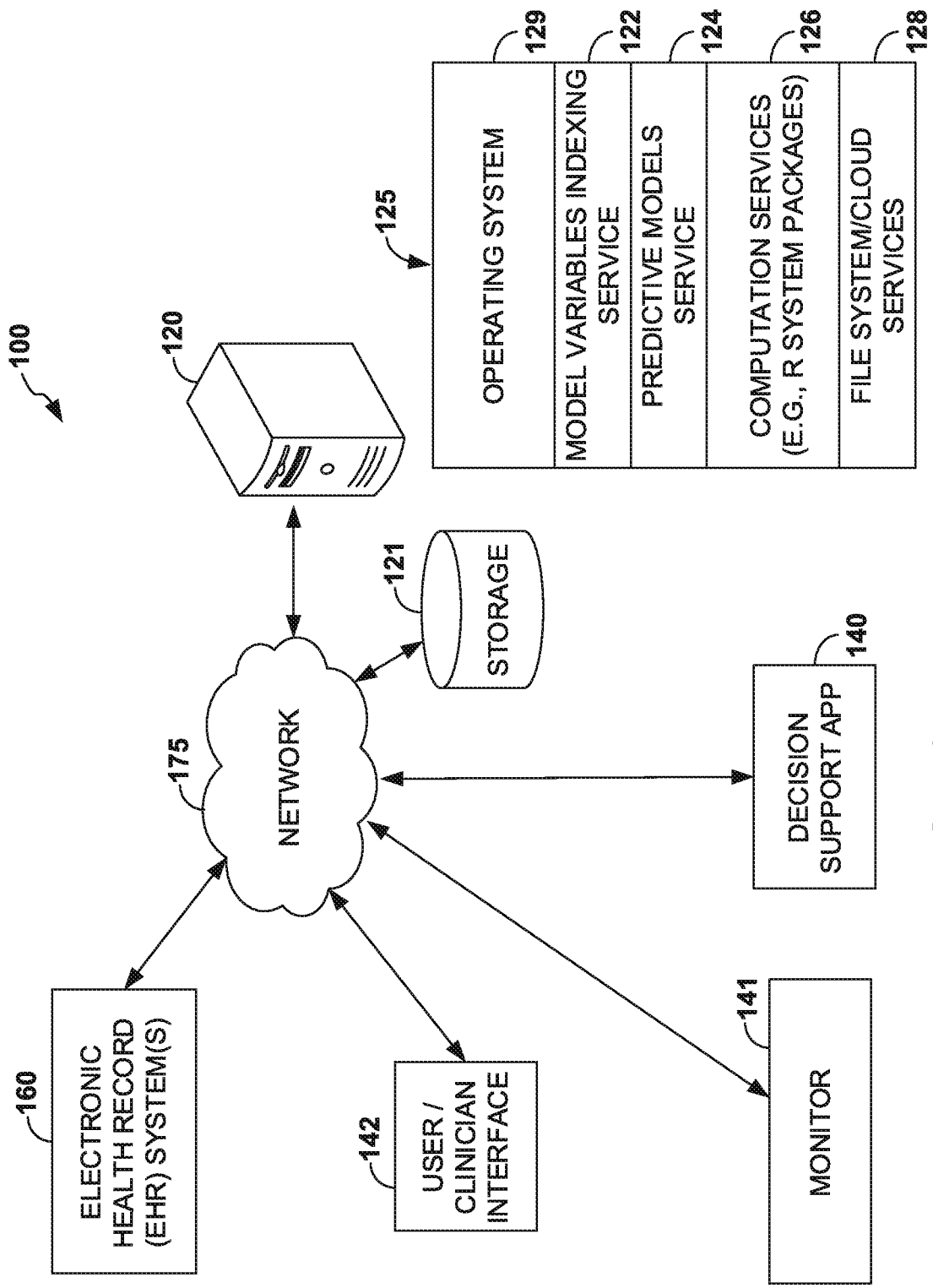
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media, as discussed further with respect to FIGS. 1A-1B.

Accordingly, at a high level, this disclosure describes, among other things, methods and systems for providing an early warning that a patient's condition is likely to deteriorate at a future time. In some embodiments, the methods and systems may be implemented as a decision support computer application or tool and may be part of a more comprehensive healthcare decision support application for monitoring patients and providing decision support to caregivers. Such decision support technology plays an important part of modern medicine. Embodiments described herein predict the occurrence of a future event indicating probable patient deterioration based on a time series of values for monitored physiological variables for a patient. Some embodiments of the decision support tool further provide advanced notice to clinicians or other caregivers when such an event is forecasted and, in some embodiments, recommend or automatically carry out modifications of a treatment for the patient according to the predicted likelihood.

In particular, embodiments include acquiring measurements for physiological variables for a patient. The measurements may be taken over a period of time and used to construct a time series for each monitored variable for the patient. Using the time series, a plurality of ratio of deviations (RoDs) may be formed for each variable. Specifically, an RoD may relate a standard deviation and a root mean square of successive differences (RMSSD) using the patient's measurements. The RoDs formed for the patient may then be used to determine a likelihood of the patient's condition deteriorating within a future time interval. In exemplary aspects, this determined likelihood is based on a Hopf bifurcation model. The RoDs for the physiological variables are used to detect a bifurcation before the patient's condition has become noticeably unstable. In some aspects, an increase in the RoD for a physiological variable corresponds to an increased likelihood of the patient deteriorating. Each variable may be assigned a score based on whether the RoD is increasing, and an aggregated score for all monitored variables may be compared to a threshold to determine the risk of the patient's condition deteriorating within a future time interval. In exemplary aspects, the future time interval is between two hours and six hours, which provides time for a clinical or other caregiver to be notified of the risk and for intervening treatments to be effective.

Accordingly, one aim of embodiments of this disclosure relates to deriving accurate and timely predictions of a patient's deterioration through an early warning system. As previously mentioned, hospitalized pediatric patients are often at risk for sudden deterioration that can lead to respiratory and/or cardiac arrest and death. Rapid response teams have been put in place at many hospitals to respond to these emergencies. Currently, many hospitals utilize a pediatric early warning system (PEWS) that quantifies subjective observations of a pediatric patient to monitor the patient's condition. Using the traditional PEWS system, a nurse or other caregiver periodically observes the pediatric patient and provides a score in different categories (e.g., behavior, cardiovascular, and respiratory) based on a scoring guide. For instance, for one observation, a nurse may observe the patient is irritable, is pale, and has respiratory values greater than 20 above the normal parameters. Utilizing a scoring chart, the nurse may score the patient with a 2 for behavior, a 1 for cardiovascular, and a 2 for respiratory. Such visual observations and chart-based scoring would periodically continue until a threshold score is reached.

This current PEWS, however, has limitations. Although the scoring chart quantifies the observations, the scores are often based on subjective characterizations of a patient (e.g., the patient's behavior and skin tone). The scores are, therefore, observer dependent and may vary based on the observer's experience. Utilizing subjective characterizations of a patient's condition may also result in even intra-observer variance. Additionally, when there is a shift change at the healthcare facility, a new observer does not have the benefit of the previous visible observations. Even if the new observer has access to the scores determined by the previous observer, the new observer may not fully appreciate the patient's previous condition based solely on another's subjective scoring.

Further, the current PEWS utilizes only the most recent data point from an actual visible observation in assigning a PEWS score. The scoring chart does not take into account changes in the measured variables even though change in a patient's condition may be a powerful indicator of a potentially rapidly deteriorating situation. Additionally, because the scoring is based on visual observations, it cannot be done on a continuous basis or in real time. Rather, observations are often performed every two to four hours, while the median time between a critical PEWS score and an event is only 30 minutes. Observing patients only every two to four hours increases the risk of a critical event occurring before the patient is next observed and scored and provides very little time for an effective preventative or therapeutic response. At the same time, a more frequent rate for visual observations is not practical due to limitations in staffing resources.

Accordingly, embodiments of the disclosure as described herein improves upon conventional industry practice by deriving accurate predictive capabilities to provide more effective treatment and care. Embodiments predict a patient's deterioration within a future interval using electronically received values for physiological variables, such as heart rate, respiratory rate, and mean arterial pressure. Measured values for these variables represent new sources of information for predicting patient deterioration that are not used in the conventional PEWS. In this way, embodiments do not rely on visual observations from a caregiver and, therefore, are not at risk for the inherent subjective biases that influences the accuracy of previous systems. Additionally, utilizing this information by automatically acquiring measurements for physiological variables does not require a caregiver to be present with the patient, which allows for continuous or on-going monitoring in real time and, consequently, earlier detection of a deterioration risk. Further, although the physiological variables used, such as heart rate, respiratory rate, and mean arterial pressure, are non-conventional sources of information in a pediatric early warning system, these variables may already be monitored and recorded for other purposes, thus eliminating or reducing the need for additional testing to determine the patient's likelihood of deterioration.

Further, the physiological variables that are used for predicting deterioration in embodiments of the disclosure are not only unconventional in an early warning system for pediatric patients, but values of those variables are used in an unconventional way to predict deterioration. In aspects herein, for instance, a ratio of deviations is formed for each physiological variable based on the Hopf bifurcation model, and a change in the ratio of deviations for each variable over time is used to forecast deterioration. Because RoD and Hopf bifurcation model do not require patient measurements to be acquired on a regular or periodic basis or at a high frequency, embodiments directed to the application of RoD and Hopf bifurcation model in the pediatric early warning system are more robust. Additionally, as described further herein, application of changes in RoD for physiological variables in the disclosed decision support tools provides a more accurate forecast for deterioration of the patient's condition within a future time to allow for effective interventions. Further, initiating response actions, such as alerts, recommendations to modify treatments, or scheduling resources, based on an RoD-based prediction of deterioration is also not conventional or well-known and may be performed with more advanced warning compared to traditional PEWS. These features improving the decision support tools for pediatric early warning systems are each unconventional and not well-known and are further unconventional in combination with one another.

Referring now to the drawings in general and, more specifically, referring to FIG. 1A, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural).

As shown in FIG. 1A, example operating environment 100 provides an aspect of a computerized system for compiling and/or running an embodiment of a computer-decision support tool for predicting likelihood of deterioration of a patient at a future time based on RoD. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or more EHR systems, such as hospital EHR systems, health information exchange EHR systems, ambulatory clinic EHR systems, and/or pediatric EHR systems. Such EHR systems may be implemented in computer system 120. Similarly, EHR system 160 may perform functions for two or more of the EHR systems (not shown).

Network 175 may comprise the Internet and/or one or more public networks, private networks, other communications networks such as a cellular network, or similar networks for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on storage 121, and may further include one or more computers or servers that facilitate storing and retrieving health records. In some embodiments, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example. Although FIG. 1A depicts an exemplary EHR system 160, it is contemplated that an embodiment relies on decision support application 140 and/or monitor 141 for storing and retrieving patient record information, such as information acquired from monitor 141.

Example operating environment 100 further includes a provider user/clinician interface 142 communicatively coupled through network 175 to EHR system 160. Although environment 100 depicts an indirect communicative coupling between user/clinician interface 142 and EHR system 160 through network 175, it is contemplated that an embodiment of user/clinician interface 142 is communicatively coupled to EHR system 160 directly. An embodiment of user/clinician interface 142 takes the form of a user interface operated by a software application or set of applications on a client computing device, such as a personal computer, laptop, smartphone, or tablet computing device. In an embodiment, the application includes the PowerChart® software manufactured by Cerner Corporation. In an embodiment, the application is a Web-based application or applet. A healthcare provider application may facilitate accessing and receiving information from a user or healthcare provider about a specific patient or set of patients for which the likelihood(s) of deterioration of the patient or set of patients at a future time are determined according to the embodiments presented herein. Embodiments of user/clinician interface 142 also facilitate accessing and receiving information from a user or healthcare provider about a specific patient or population of patients including patient history; healthcare resource data; physiological variables (e.g., vital signs), measurements, time series, and predictions (including plotting or displaying the determined outcome and/or issuing an alert) described herein; or other health-related information, and facilitates the display of results, recommendations, or orders, for example. In an embodiment, user/clinician interface 142 also facilitates receiving orders for the patient from the clinician/user based on the results of monitoring and predictions. User/clinician interface 142 may also be used for providing diagnostic services or evaluation of the performance of various embodiments.

An embodiment of decision support application 140 comprises a software application or set of applications (which may include programs, routines, functions, or computer-performed services) residing on a client computing device, on one or more servers in the cloud, or distributed in the cloud and on a client computing device such as a personal computer, laptop, smartphone, tablet, mobile computing device, front-end terminals in communication with back-end computing systems, or other computing device(s) such as computing system 120 described below. In an embodiment, decision support application 140 includes a Web-based application or set of applications usable to manage user services provided by an embodiment of the invention. For example, in an embodiment, decision support application 140 facilitates processing, interpreting, accessing, storing, retrieving, and communicating information acquired from monitor 141, EHR system 160, or storage 121, including predictions and condition evaluations determined by embodiments of the invention as described herein. In an embodiment, decision support application 140 sends a notification (such as an alarm or other indication) directly to user/clinician interface 142 through network 175. In an embodiment, decision support application 140 sends a maintenance indication to user/clinician interface 142. In one embodiment of decision support application 140, an interface component may be used to facilitate access by a user (including a clinician/caregiver or patient) to functions or information on monitor 141, such as operational settings or parameters, user identification, user data stored on monitor 141, and diagnostic services or firmware updates for monitor 141, for example.

As shown in example environment 100, in one embodiment, decision support application 140 is communicatively coupled to monitor 141 via network 175. In an embodiment, patient monitor 141 communicates directly (or via network 175) to computer system 120 and/or user/clinician interface 142.

In an embodiment, monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient. Such clinical or physiological information may be acquired by monitor 141 periodically, continuously, as needed, or as they become available, and may be represented as one or more time series of measured variables. In one embodiment, monitor 141 comprises sensors for obtaining (and, in some instances, pre-processing or interpreting) and recording vital signs, which may be obtained continuously, periodically, or at irregular intervals. For example, in an embodiment, monitor 141 comprises a patient monitoring system for acquiring commonly available vital signs (physiological variables) such as respiratory rate, heart rate, and mean arterial pressure (blood pressure). In some embodiments, monitor 141 comprises patient bedside monitor, such monitors used in hospitals. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about the patient, such as the monitored variables and/or clinical narratives regarding the patient, used according to the embodiment of the invention disclosed herein may be received from a patient's historical data in EHR system 160, or from human measurements, human observations, or automatically determined by sensors in proximity to the patient. For example, in one embodiment, a nurse periodically measures a patients' blood pressure and enters the measurement and/or observations via decision support application 140 or interface 142. In another example, a nurse or caregiver enters one or more progress notes for a patient via decision support application 140 or user/clinician interface 142. Similarly, values for vital sign variables may be entered via decision support application 140 or user/clinician interface 142.

Examples of physiological variables monitored by monitor 141 can include vital sign variables, such as heart rate (bradycardia and tachycardia), blood pressure (hypotension and hypertension), and respiratory rate, as described herein. Additionally, in some embodiments, physiological variables monitored by monitor 141 may include, by way of example and not limitation, central venous pressure, other vital signs or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient to facilitate clinical decision making In an embodiment, monitor 141 comprises a sensor probe, such as an EEG probe, and a communication link that periodically transmits identification information and probe data to decision support application 140 so that the time series of monitored values is stored on decision support application 140, enabling patient decision support application 140 to form a raw binary alarm indication and/or a physiological variable decision statistic. In an embodiment, patient monitor 141 collects raw sensor information and performs signal processing, forming a physiological variable decision statistic, cumulative summing, trending, wavelet processing, thresholding, computational processing of decision statistics, logical processing of decision statistics, pre-processing or signal condition, etc., part or all of which may be performed on monitor 141, decision support application 140, user/clinician interface 142, and/or computer system 120.

An embodiment of monitor 141 stores user-derived data locally or communicates data over network 175 to be stored remotely. In an embodiment, decision support application 140 is wirelessly communicatively coupled to monitor 141. Decision support application 140 may also be embodied as a software application or app operating on a user's mobile device. In an embodiment, decision support application 140 and monitor 141 are functional components of the same device, such as a device comprising a sensor and a user interface. In an embodiment, decision support application 140 is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121.

Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations such as one or more local clients and one or more remote servers and may be distributed across the other components of example operating environment 100. For example, a portion of computer system 120 may be embodied on monitor 141 or decision support application 140 for performing signal conditioning of the measured patient variable(s). In one embodiment, computer system 120 comprises one or more computing devices, such as a server, desktop computer, laptop, or tablet; cloud-computing device or distributed computing architecture; a portable computing device such as a laptop, tablet, ultra-mobile P.C.; or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud and is capable of hosting a number of services such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running interface 140 and/or patient manager 142. In some embodiments, user/clinician interface 142 operates in conjunction with software stack 125.

In embodiments, model variables indexing service 122 provides services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, model variables indexing service 122 may invoke computation services 126. Predictive models service 124 is generally responsible for providing multi-variable models for predicting near-term occurrence (early warning) of patient deterioration based on sparse observations, such as the RoD-based approach described in connection to method 200 of FIG. 2.

Computation services 126 perform statistical software operations and include statistical calculation packages such as, in one embodiment, the R-System (the R-project for Statistical Computing, which supports R-packages or modules tailored for specific statistical operations and which is accessible through the Comprehensive R Archive Network (CRAN) at cran.r-project.org) or similar services. In an embodiment, computation services 126 and predictive models service 124 include computer software services or computer program routines such as the example embodiments of computer program routines illustratively provided in FIGS. 10A-10C. In one embodiment, computation services 126 comprises the R-System modules or packages foreach and doParallel, for parallel processing to speed up computation of future trajectories and deSolve for solving differential equations to simulate various trajectories. In an embodiment, computation services 126 and predictive models service 124 include the services or routines that may be embodied as one or more software agents or computer program routines, such as the example computer program routines of FIGS. 10A-10C.

In some embodiments, stack 125 includes file system or cloud-services 128. Some embodiments of file system/cloud-services 128 may comprise an Apache Hadoop and Hbase framework or similar frameworks operable for providing a distributed file system and which, in some embodiments, provide access to cloud-based services such as those provided by Cerner Healthe Intent®. Additionally, some embodiments of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which, in some embodiments, includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and itemsets index information; association rulebases; agent libraries, solvers and solver libraries, and other similar information including data and computer-usable instructions; patient-derived data; and healthcare provider information, for example. It is contemplated that the term "data" used herein includes any information that can be stored in a computer-storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

Figure 1B:
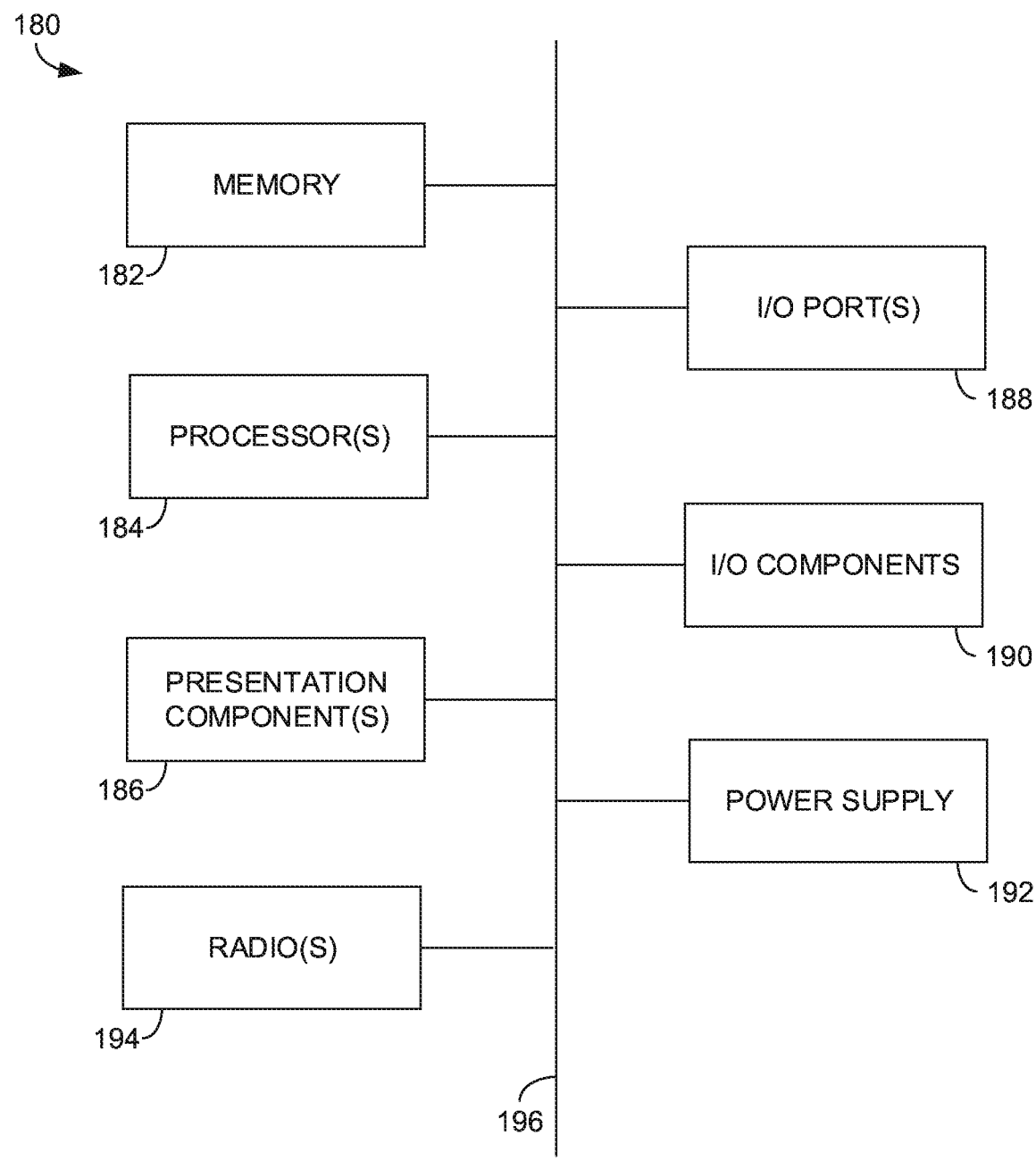

Turning briefly to FIG. 1B, there is shown one example embodiment of computing system 180 representative of a system architecture that is suitable for computer systems such as computer system 120. Computing device 180 includes a bus 196 that directly or indirectly couples the following devices: memory 182, one or more processors 184, one or more presentation components 186, input/output (I/O) ports 188, input/output components 190, radio 194, and an illustrative power supply 192. Bus 196 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an exemplary computing system that can be used in connection with one or more embodiments of the present invention. Distinction is not made between such categories as "workstation,"

"server," "laptop," "hand-held device," etc., as all are contemplated within the scope of FIG. 1B and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 182 includes computer-storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 182 or I/O components 190. Presentation component(s) 186 present data indications to a user or other device. Exemplary presentation components include a display device, speaker, printing component, vibrating component, etc.

In some embodiments, computing system 194 comprises radio(s) 194 that facilitates communication with a wireless-telecommunications network. Illustrative wireless telecommunications technologies include CDMA, GPRS, TDMA, GSM, and the like. Radio 194 may additionally or alternatively facilitate other types of wireless communications including Wi-Fi, WiMAX, LTE, or other VoIP communications. As can be appreciated, in various embodiments, radio 194 can be configured to support multiple technologies and/or multiple radios can be utilized to support multiple technologies.

I/O ports 188 allow computing system 180 to be logically coupled to other devices, including I/O components 190, some of which may be built in. Illustrative components include a microphone, joystick, game pad, satellite dish, scanner, printer, wireless device, etc. The I/O components 190 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer, or a networked computing system.

Figure 2:
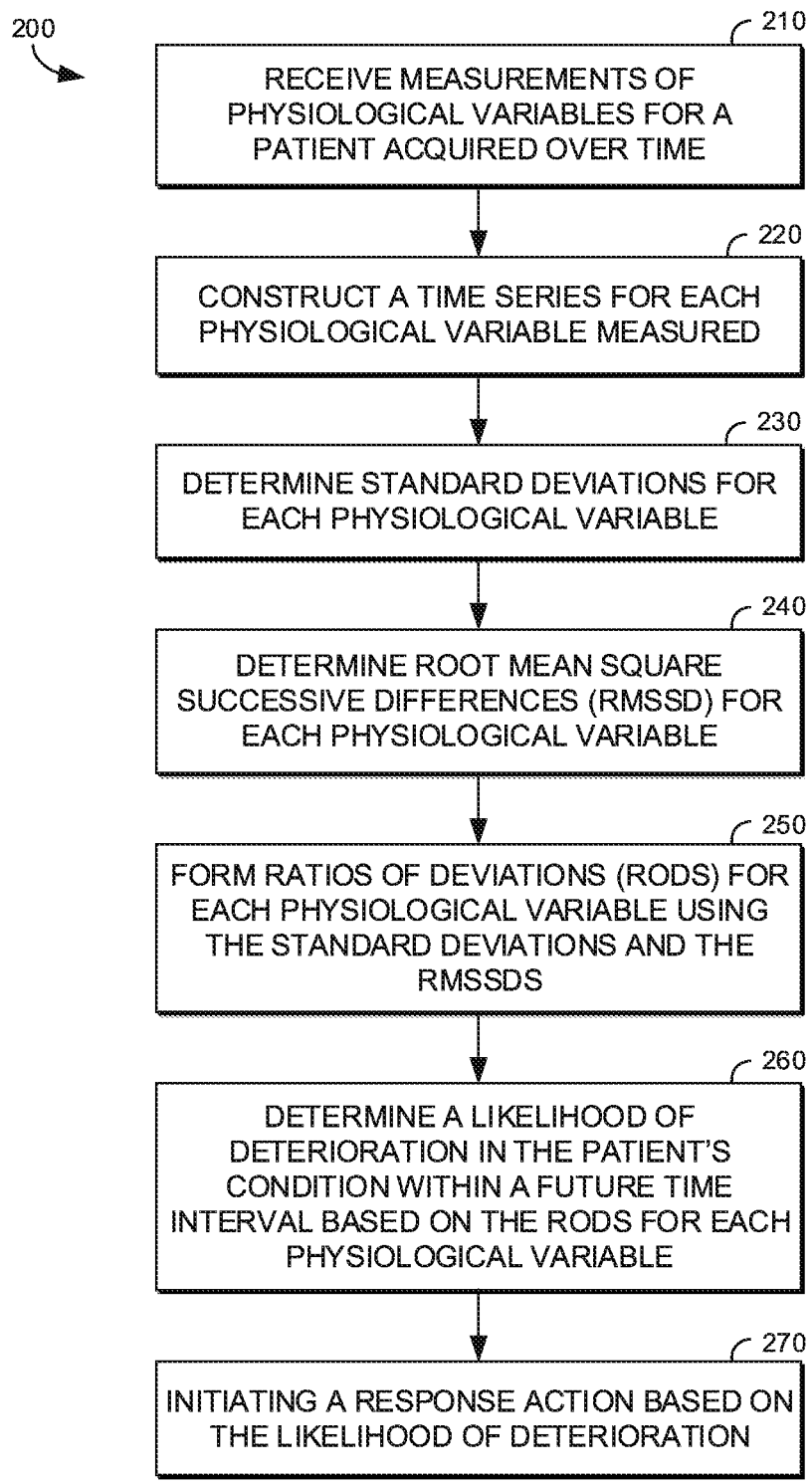
FIG. 2 depicts a flow diagram of a method for predicting likely deterioration of a patient's condition during a future time interval based on ratios of deviations and suitable for implementation in an early warning decision support system, in accordance with an embodiment of the disclosure.

Turning now to FIG. 2, one example embodiment of a method for predicting deterioration of a patient's condition for a future time interval is provided and is referred to generally as method 200. In particular, example method 200 utilizes ratios of deviations for determining the probability of a future event, such as a bifurcation indicating deterioration. In some embodiments, method 200 is suitable for implementation as a computer-performed decision support tool or application for providing early warning of patient deterioration and, thus, increasing the odds of patient survival by enabling caregivers to intervene sooner than conventional technology would otherwise allow. In some embodiments, aspects of method 200 may be carried out using the example computer program routine depicted in FIGS. 10A-10C.

Figure 3A:
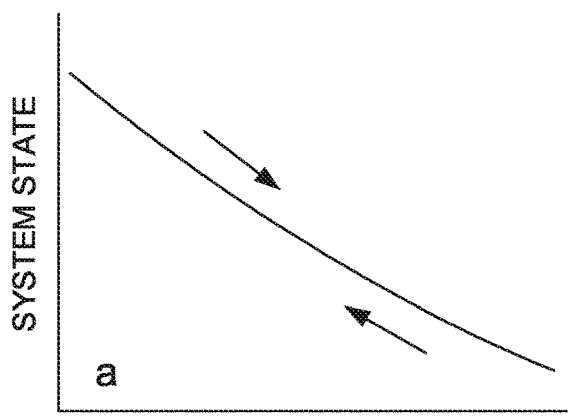
FIGS. 3A-3C each depict a graphical illustration of a type of transition in a system state.
Figure 3B:
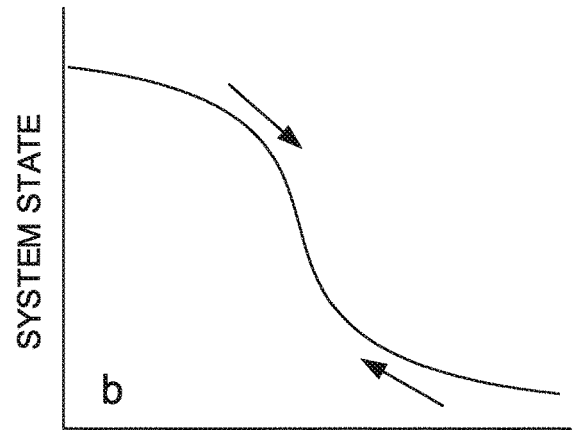
Figure 3C:
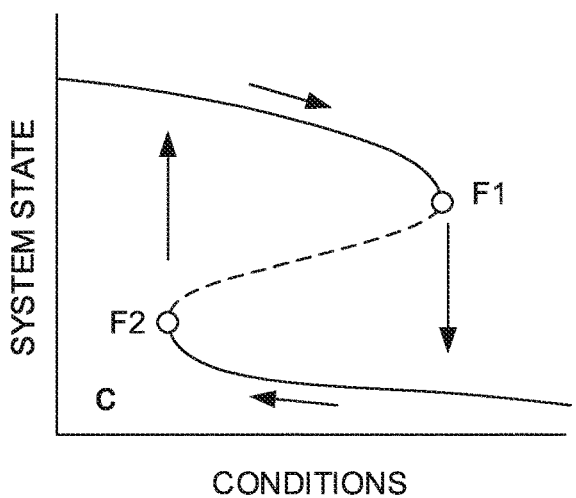

With reference to FIG. 2 and method 200, generally, the method 200 of predicting deterioration of a patient's condition for a future time interval utilizes ratio of deviations to detect a bifurcation event. Bifurcation represents a change in a system. FIGS. 3A-3C illustrate some basic types of transitions within a system as a condition within the system changes. FIG. 3A depicts a transition with a gradual, continuous slope such that the system experiences gradual changes as the condition changes. FIG. 3B depicts another system experiencing at least a sudden change represented by the more pronounced slope. The transitions in FIGS. 3A and 3B are reversible such that as the condition reverts back to a previous state, the system may also revert to a previous state. FIG. 3C, however, represents a sudden and irreversible transition. In mathematics, a sudden and irreversible change in the state of a system is called a critical transition or a catastrophic bifurcation. These changes have a tipping point (i.e., a "point of no return"), which is represented by point F1 in FIG. 3C.

Figure 4A:
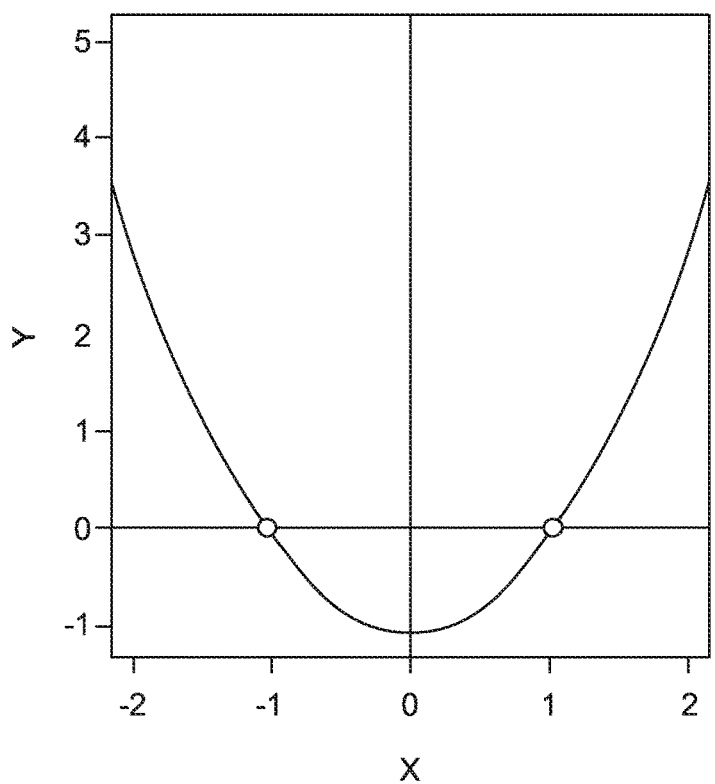
FIGS. 4A-4E depict graphical illustrations of an example bifurcation.
Figure 4B:
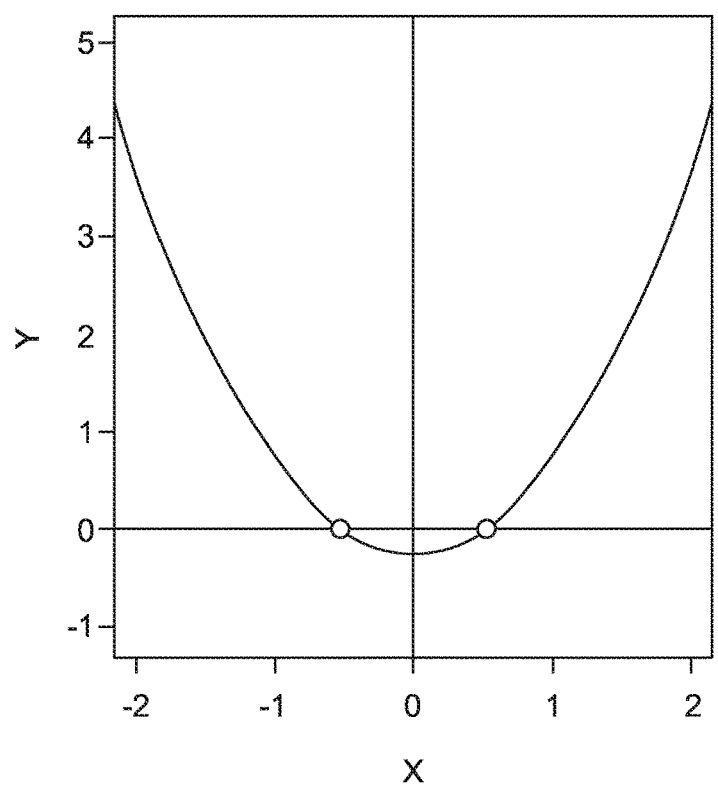
Figure 4C:
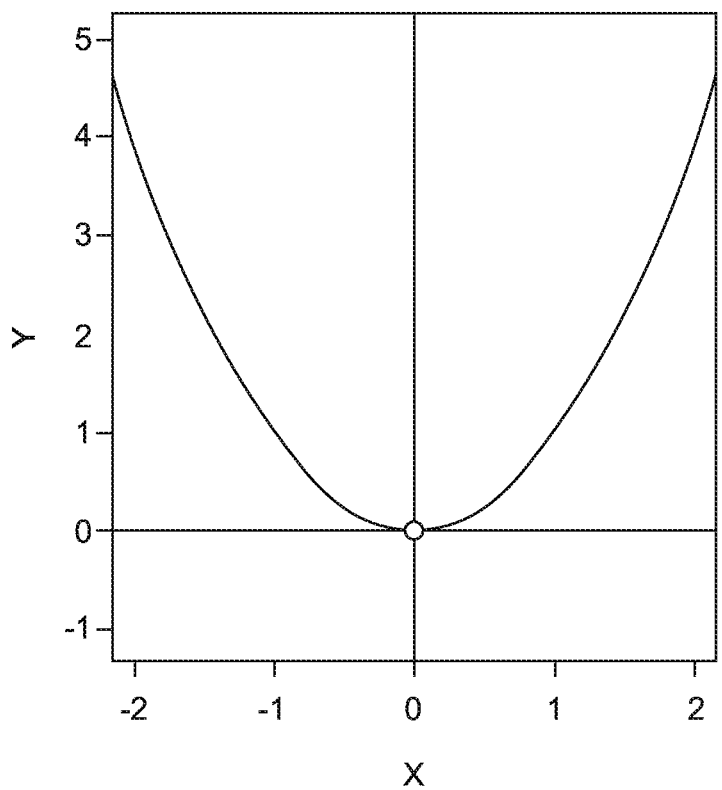
Figure 4D:
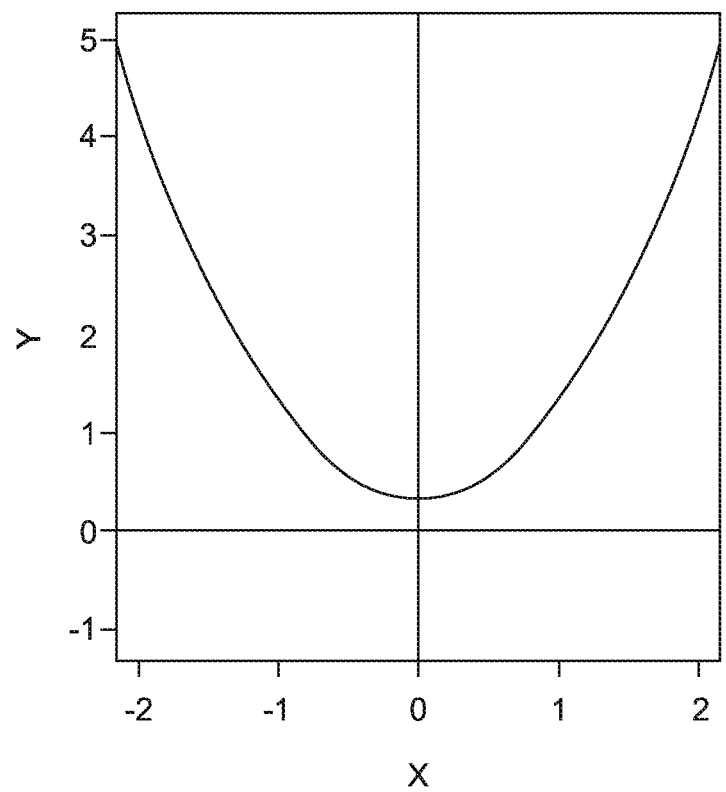
Figure 4E:
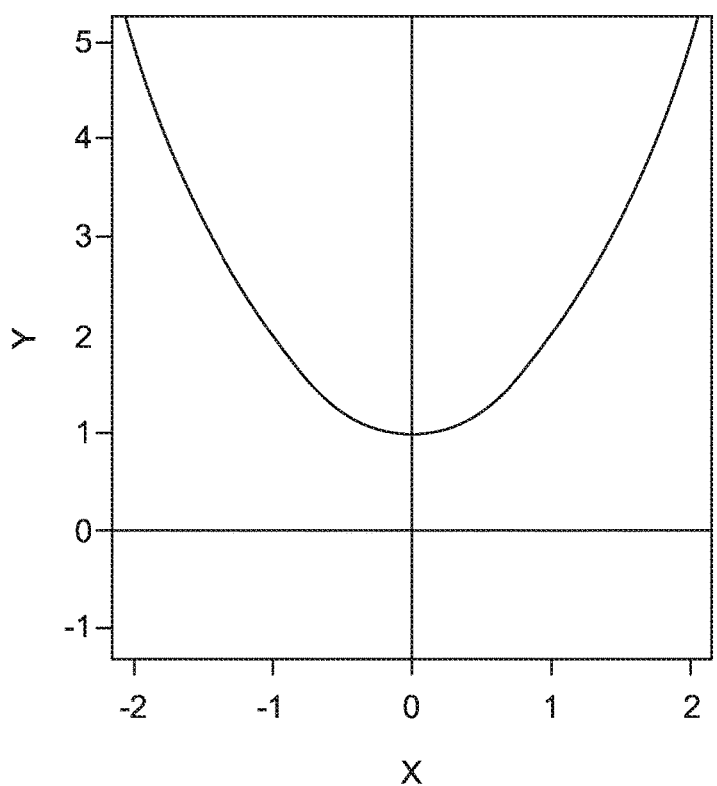
Figure 5A:
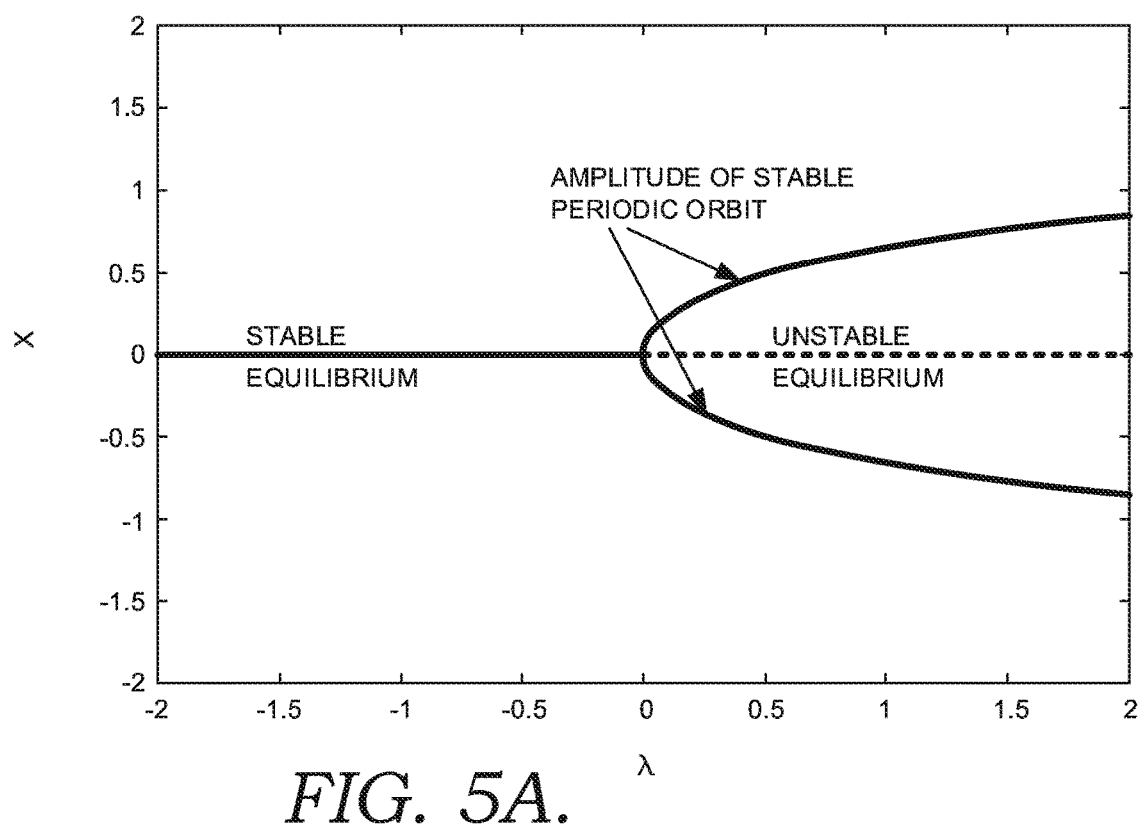
FIGS. 5A-5D depict graphical illustrations of an example supercritical Hopf bifurcation in a dynamical system.
Figure 5B:
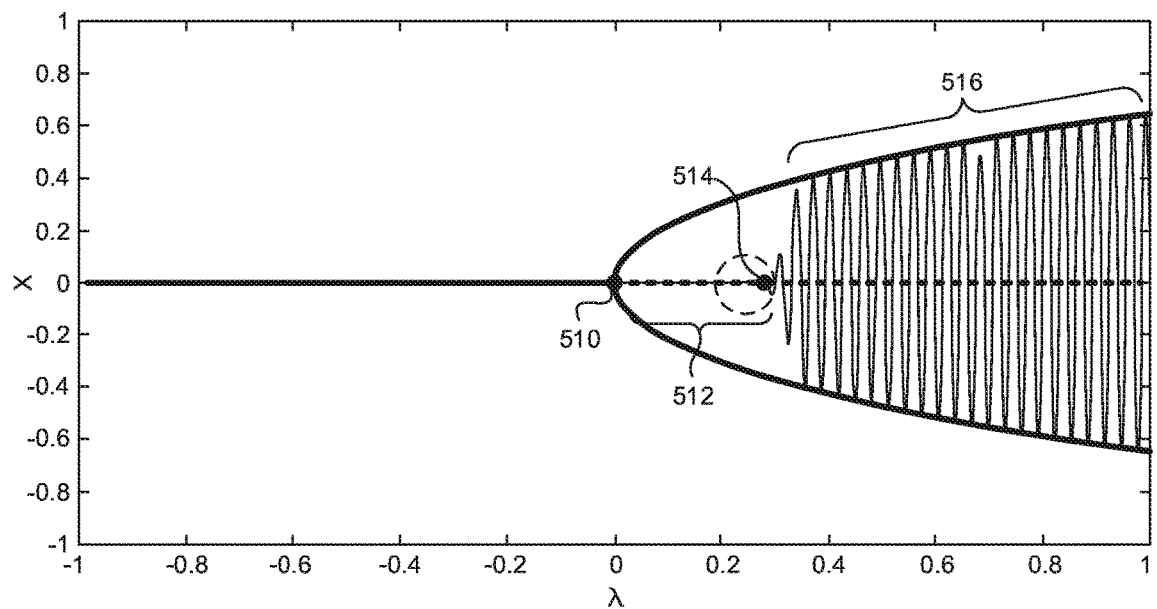
Figure 5C:
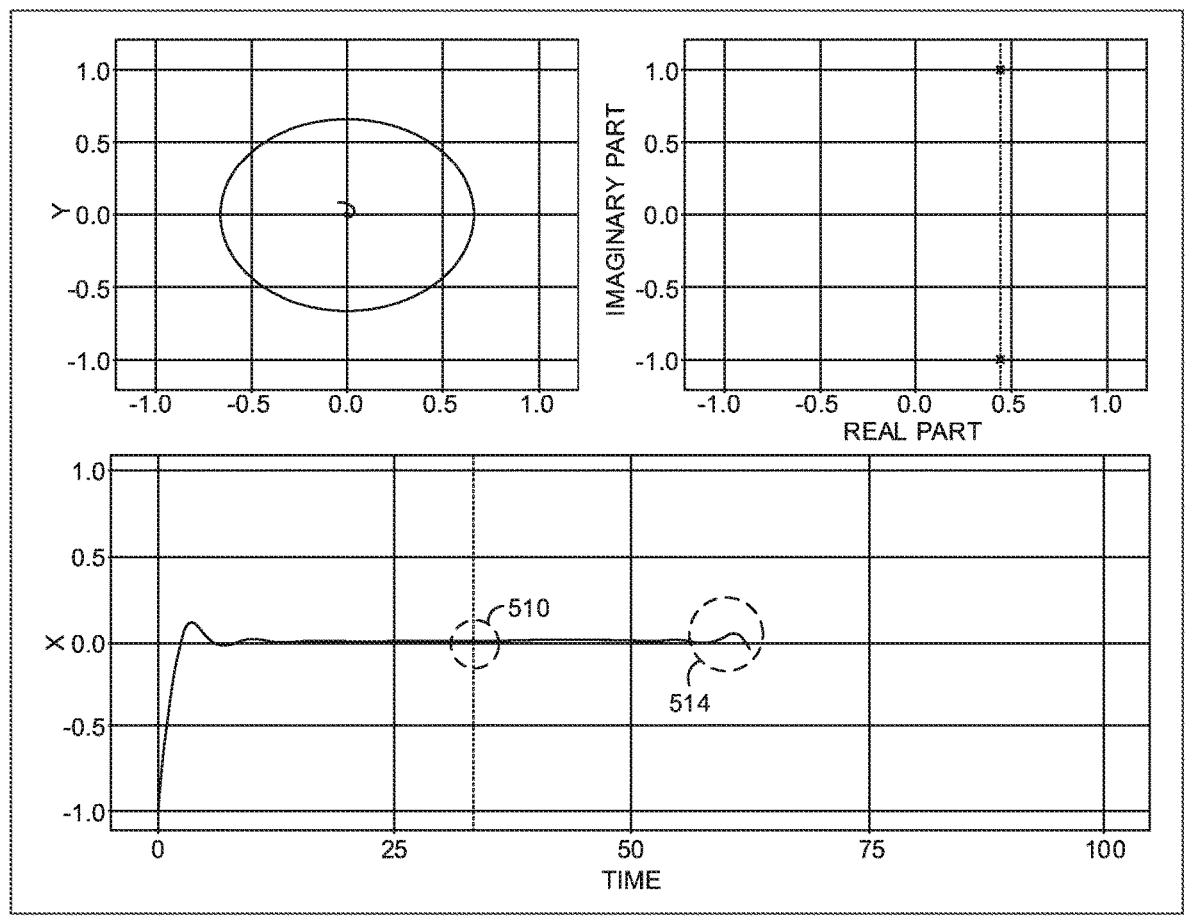
Figure 5D:
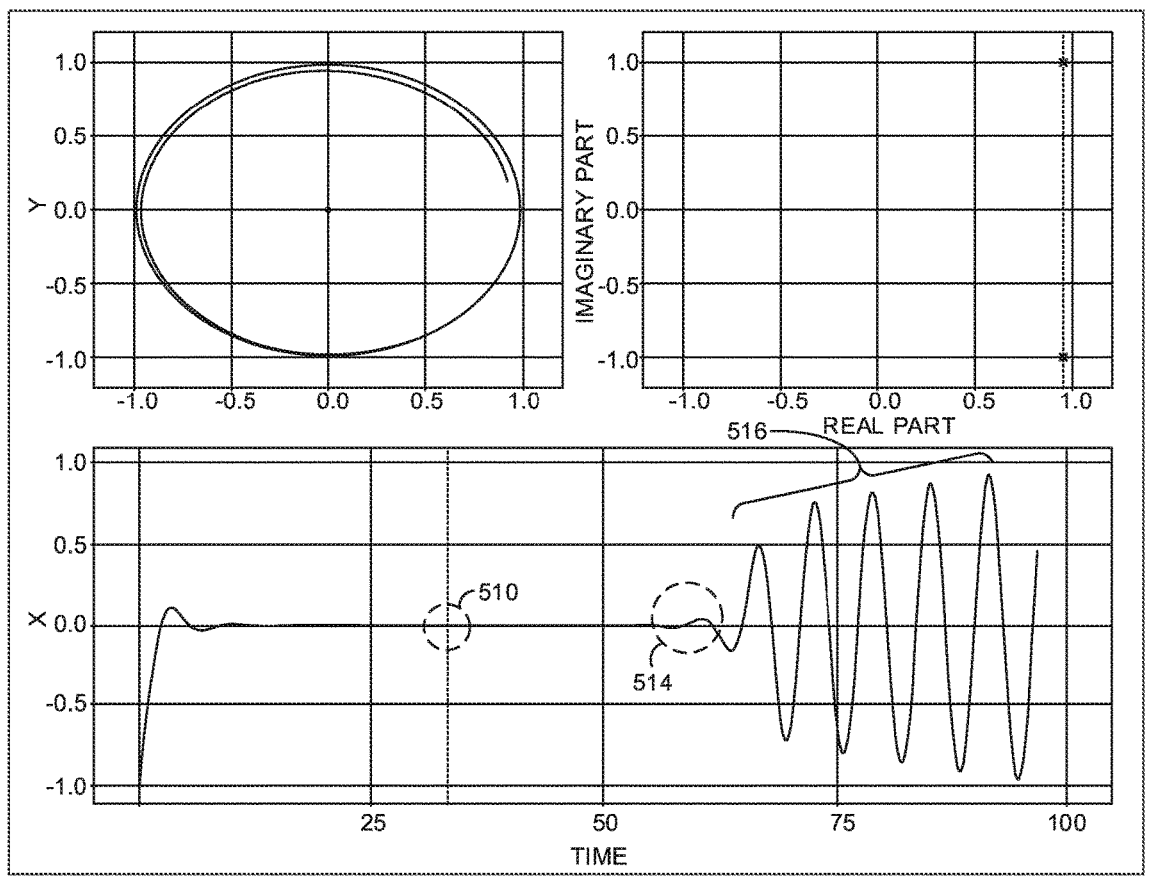

A bifurcation is a change in the number or nature of solutions. FIGS. 4A-4E provide a graphical illustration of an example bifurcation using the quadratic equation. In this example, bifurcation occurs when the discriminant changes sign. For example, in FIG. 4A, the discriminant equals four and, consequently, there are two real solutions. In FIG. 4B, the discriminant equals one, and there are still two real solutions. In FIG. 4C, the discriminant equals zero, and there is only one real solution. FIG. 4C represents the bifurcation point because the number of solutions has changed. In FIG. 4D, the discriminant is negative one, and there are no real solutions. At this point, bifurcation is complete. As the discriminant continues in the same trend and is negative four, there are still zero solutions, as shown in FIG. 4E.

While some bifurcations are catastrophic (irreversible), other types of bifurcations, such as a supercritical Hopf bifurcation, are reversible and, thus, do not have an actual tipping point. A Hopf bifurcation is a critical point where a system's stability changes and a periodic solution arises. Such bifurcations still involve the deterioration of a stable state, and even though they are not technically irreversible, it is often difficult to reverse the system in practice. Accordingly, in many applications, such as clinical conditions of pediatric patients, it is still desirable to identify the changes in stability, such as a Hopf bifurcation.

A Hopf bifurcation occurs when the change in stability of an equilibrium coincides with either the emergence or disappearance of a periodic orbit. A subcritical Hopf bifurcation occurs where the periodic orbit exists before the bifurcation point and includes three stages: (1) a strongly stable equilibrium coexisting with an unstable periodic orbit; (2) weakly unstable equilibrium; and (3) strongly unstable equilibrium. A supercritical Hopf bifurcation, on the other hand, occurs where the periodic orbit exists after the bifurcation point and comprises the following stages: (1) strongly stable equilibrium point; (2) weakly stable equilibrium point; and (3) unstable equilibrium point with stable periodic orbit. Although aspects described herein may apply to a subcritical bifurcation, a supercritical bifurcation is depicted in FIGS. 5A-5D. As shown in FIGS. 5A-5D, when lambda is less than 0, there is a stable equilibrium state. At 0, there is a weakly stable equilibrium point, which is the bifurcation point 510. As lambda is greater than 0, there is an unstable equilibrium, represented by the dashed line, and a stable periodic orbit 516 around the unstable equilibrium point. The periodic orbit 516 is sometimes referred to herein as spiraling out. The maximum and minimum x values of the periodic orbit 516 are indicated as the amplitude of stable periodic orbit curves in FIG. 5A.

In the context of a patient's physiological state, the level of stress on a patient's body may be determined over time using one or more physiological variables, such as respiratory rate, heart rate, and blood pressure. Such level may determine the equilibrium state, and how sick a patient is may determine the equilibrium state and whether or not such a state is stable. At times, the patient may be able to compensate for certain stresses. As the patient's condition deteriorates, however, there may reach a point, such as bifurcation point 510, in which the patient can not compensate normally and the patient's vitals (the physiological variables) may spiral out of control, which may lead to critical conditions such as cardiac arrest.

In dynamic Hopf bifurcation, there is a hysteresis effect in that the trajectory may remain near the newly unstable equilibrium for some time before the periodic orbit occurs. The hysteresis effect 512 is the period of "stable" instability between the bifurcation point 510 and a point 514 at which the periodic orbit begins (also referred to herein as the deterioration point). During the time of the hysteresis effect 512, there may be small oscillations, but these small oscillations are less detrimental and easier to reverse than the larger oscillations within the periodic orbit 516. Because of the hysteresis effect, there may be time to prevent the periodic orbits 516 even if the bifurcation point 510 is not detected until after it has occurred. Reversing the bifurcation after it nears the periodic orbit, however, may still require a significant change in the parameters, such as a patient's physiological variables.

To detect a Hopf bifurcation and predict a likelihood of the patient's condition deteriorating within a future time interval, a ratio of deviations (RoD) is determined for a plurality of measured physiological variables. RoD may be defined as a root mean square of successive differences (RMSSD) divided by the standard deviation. For instance, Let $X_{tk}$ be a univariate time series where k=1, . . . , n, . . . . The RoD relates the RMSSD, v, and the standard deviation, σ, as provided in the equations below:

$$v^2(t_n) = \frac{1}{n-1} \sum_{i=2}^{n} (X_{t_i} - X_{t_{i-1}})^2 \quad (1)$$

$$\sigma^2(t_n) = \frac{1}{n} \sum_{i=1}^{n} (X_{t_i} - \mu_n)^2 \quad (2)$$

where μ=E[X]. RoD is defined as $$RoD(t_n) = \frac{v(t_n)}{\sigma(t_n)} \quad (3)$$

An increase in RoD may indicate a change in the nature of oscillations such that RoD predicts passage through a Hopf bifurcation, including passage though the bifurcation point 510 and the deterioration point 514. As used in embodiments wherein, the change in oscillations indicates a patient's condition is deteriorating. RoD may be used instead of autocorrelation to detect bifurcation. Autocorrelation is a measure of how similar values in a times series are to values that proceed them. For instance, high autocorrelation means high values are likely to be followed by more high values where low autocorrelation means high values are likely to be followed by low values, for example. Autocorrelation has been used as an early warning signal for catastrophic bifurcations in contexts outside the pediatric warning system. However, in addition to other deficiencies described herein, autocorrelation can only detect the change in oscillations when the periodicity or lag is known, which is unlikely in the context of monitoring pediatric patients.

In accordance with some aspects herein, if $X_{t_i}$ is a weakly stationary process, which is one that requires $$\lim_{n \to \infty} \sigma^2(t_n) < \infty$$

such that the time series is convergent, then $$\lim_{n \to \infty} RoD^2(t_n) = 2(1 - \rho_x(1)), \quad (4)$$

where $p_x(1)$ is the lag-1 autocorrelation of $X_{t_i}$.

To prove this proposition, consider that both standard deviation and RMSSD are independent of the mean, so it may be assumed that E[X]=0 without the loss of generality. Since $X_{t_i}$ is weakly stationary, the following is true:

$$\rho x(1) = \frac{E[X_{t_i} X_{t_{i-1}}]}{\sigma^2}$$

Thus, $$\lim_{n \to \infty} RoD^2(t_n) = \lim_{n \to \infty} \frac{\frac{1}{n-1}\sum_{i=2}^{n}(X_{t_i} - X_{t_{i-1}})^2}{\frac{1}{n}\sum_{i=1}^{n}X_{t_i}^2}$$

$$= \lim_{n \to \infty} \frac{\frac{1}{n-1}\sum_{i=2}^{n}X_{t_i}^2 + \frac{1}{n-1}\sum_{i=1}^{n-1}X_{t_i}^2 - 2\frac{1}{n-1}\sum_{i=2}^{n}X_{t_{i-1}}X_{t_i}}{\frac{1}{n}\sum_{i=1}^{n}X_{t_i}^2}$$

$$= \lim_{n \to \infty} \left( \frac{\frac{1}{n-1}\sum_{i=2}^{n}X_{t_i}^2}{\frac{1}{n}\sum_{i=1}^{n}X_{t_i}^2} + \frac{\frac{1}{n-1}\sum_{i=1}^{n-1}X_{t_i}^2}{\frac{1}{n}\sum_{i=1}^{n}X_{t_i}^2} - 2\frac{\frac{1}{n-1}\sum_{i=2}^{n}X_{t_{i-1}}X_{t_i}}{\frac{1}{n}\sum_{i=1}^{n}X_{t_i}^2} \right)$$

$$= 2\frac{\sigma^2}{\sigma^2} - 2\rho x(1)$$

$$= 2(1 - 2\rho x(1))$$

Accordingly, it cannot be concluded that for sufficiently long time series, the following exists:

$$RoD^2 \approx 2(1-2\rho x(1)) \quad (5)$$

An AR(1) coefficient and RoD may be computed for any finite time series; however, the result may rely on $\sigma^2$ (eventually) being time-independent.

By examining a ratio of two distinct measures of dispersion, RoD may detect a change in the nature of deviations in a time series. Specifically, RoD detects a change in the variable $X_t$ at time $t_k$ when $RoD(t_k)>RoD(t_{k-1})$. Only a single increase in RoD is required to detect the change in contrast with the standard practice for other early warning signals, such as autocorrelation, which requires an increasing trend. Accordingly, RoD, which detects a change in the nature of jumps in a time series, is better for detection with low-frequency observations (with long periods of time between observations) than autocorrelation and provides a clear application for higher dimensions, such as with multiple variables. Another benefit of RoD over autocorrelation is that it may be used with non-uniform observation rates in which there is a large variation in the time between observations, whereas autocorrelation requires a known lag and performs better with uniform periods. RoD may be also used with high-frequency observations by sampling techniques.

In some embodiments, RoD may be paired with a tandem value to increase the accuracy of detected bifurcations. In exemplary aspects, the tandem value is the standard deviation; however, it is contemplated that other values, such as RMSSD, may also be used. The tandem metric used may depend on the application, a priori knowledge of the underlying system, or properties of the observations (especially on short time series). In other embodiments, to reduce the number of false positives, a restriction on the range of values a given physiological variable can take is set, and a value not meeting those restrictions is required before a critical point is detected.

For a univariate time series $X_t$, the underlying model may be assumed to be of the form:

$$X_{t_k} = a_{t_k} X_{t_k} + \xi_{t_k} \quad (6)$$

A change in $a_t$ will affect the stability of the system, possibly causing an increase in RoD depending on the magnitude and direction of the change. Alternatively, RoD could detect a change due to a rare event where $\xi_{t_k}$ takes a value far from its mean.

Because deterioration detection may be triggered due to a random event rather than deterioration of a stable state, in some aspects, RoD is applied to multivariate systems. Consider the multivariate linear system:

$$\vec{X}(t_k) = A(t_k)\vec{X}(t_{k-1}) + \vec{\xi}_{t_k} \quad (7)$$

where, $\vec{X}(t) = (X_1(t), \ldots, X_n(t)) \in \mathbb{R}^2$, $\vec{\xi}(t) = (\vec{\xi}_1(t), \ldots, \vec{\xi}_n(t)) \in \mathbb{R}^2$, and $A(t) = (a_{ij}(t))$.

By calculating the RoD for each variable $X_i(t)$ individually, we are able to detect changes in particular subsystems. If a change is detected in only one variable, it may be attributable to a noise term. However, if a change is detected in all variables (or all variables of a subsystem), it is likely indicative of a structural change in the system. Furthermore, in embodiments in which RoD is used on short time series with long times between observations, the effects of noise may be expected to subside before the next observation if the system were stable. Accordingly, in some aspects herein, a patient's measurements for multiple physiological variables, such as respiratory rate, heart rate, and mean arterial pressure, are measured and used to determine an RoD, rather than rely on a single variable.

Note that the changes are detected by observing an increase in the RoD of each univariate time series. An increase in the RoD may roughly correspond with a decrease in autocorrelation. If the underlying system loses stability due to decreasing autocorrelation, the trajectory would be expected to develop oscillations of increasing amplitude. Thus, RoD is an appropriate mechanism for detecting Hopf bifurcations.

In light of the foregoing and turning back to method 200 of FIG. 2, an embodiment for utilizing RoD as an early warning signal for predicting a patient's deterioration at a future time interval is provided. First, at step 210, a plurality of measurements of physiological variables for a patient is received. The plurality of measurements may have been acquired for the patient period of time. In exemplary aspects, the physiological variables include respiratory rate, heart rate, and mean arterial pressure (blood pressure). Using all three variables together increases the accuracy of this early warning method because it reduces the risk of false positives. If one or even two of these variables are at sub-optimal levels, it is not necessarily a signal of bifurcation occurring. For instance, if a patient is having difficulty breathing, the respiratory rate may be outside of the normal range, and the patient's heart rate may also be abnormal due to the patient's heart may working to compensate for the respiratory problems. These issues may not necessarily be sufficiently serious to indicate a critical deterioration of the patient's condition. However, when considering all three of respiratory rate, heart rate, and blood pressure, the detected changes using the RoD are more likely to be indicative of bifurcation (i.e., deterioration to an instable state). These example variables are not intended to be limiting as it is contemplated that other physiological variables may be used. Additionally, in some embodiments, there may be more than three physiological variables monitored.

The measurements for the physiological variables may be received from the patient's EHR, such as a medical EHR within EHR system 160 in FIG. 1, or other data storage, or may be received directly from a monitoring device, such as patient monitor 141. In some aspects, the physiological variables are being monitored independently of the early-warning signal system. In other words, rather than require additional testing or acquisition of additional data to perform method 200, method 200 may leverage data that is often already being recorded in the normal course of monitoring and treating a patient, such as heart rate, respiratory rate, and blood pressure, to detect deterioration of the patient within a future time interval. Embodiments of step 210 may acquire the vital signs measurements continuously, periodically, or at non-regular intervals. In some embodiments, the date/time information for each measurement is stored with the measured variable values.

Next, as step 220, a time series from the plurality of measurements is constructed for each physiological variable measured. The time series may be constructed by appending the most recent physiological variable measurements to the historical measurements, using the associated date/time information. In some embodiments, the historical measurements comprise measurements obtained within a recent timeframe such as the previous several hours, last six hours, the previous day, or the previous week. In such embodiments, only historical measurements from within this recent timeframe are retrieved and used for the constructing time series. In some aspects, the time series is evaluated to determine whether it is of sufficient length. In one embodiment, where the time series is determined to be greater than a pre-determined length, method 200 proceeds to step 230. But if the time series is not long enough, then method 200 returns to step 210 where additional measurements may be acquired. In one embodiment, the pre-determined length comprises six samples.

At step 230, a plurality of standard deviations for each physiological variable is determined based on the constructed time series. Standard deviation may be calculated using equation (2) provided above. Similarly, a plurality of root mean square of successive differences (RMSSDs) for each physiological variable is determined at step 240. The RMSSDs may be calculated in accordance with equation (1) provided above. Then, at step 250, the RoD for each physiological variable is formed using equation (3) provided above. Specifically, the RoD is found by dividing the RMSSD with the respective standard deviation. Accordingly, in embodiments in which the physiological variables comprise heart rate, respiratory rate, and blood pressure, an RoD for blood pressure is formed by dividing the RMSSD for blood pressure measurements over the standard deviation for the blood pressure measurements; an RoD for heart rate is formed by dividing the RMSSD for heart rate measurements over the standard deviation for the heart rate measurements; and an RoD for respiratory rate is formed by dividing the RMSSD for respiratory rate measurements over the standard deviation for the respiratory rate measurements.

In aspects, the RoD for each variable is determined multiple times throughout the time series. Accordingly, there may be an RoD determined at t=10 and an RoD for the same variable at t=20. Based on these RoDs, the variable will be given an RoD score, which indicates a change in the RoD for that variable. In some aspects, the RoD score is either "0" or "1", with a score of "1" being given when the RoD for a variable has increased when compared to the RoD of an earlier time. Accordingly, each physiological variable may be assigned an RoD score that is either a "0" or a "1".

Once the RoD score is assigned for each physiological variable, at step 260, a likelihood of deterioration in the patient's condition within a future time interval is determined. In some embodiments, the future time interval is within a range of thirty minutes to twenty hours. For example, the RoD scores may be used to predict a patient has a likelihood of deteriorating within eight hours. The future time interval may comprise other time intervals in other embodiments.

In some aspects, determining the likelihood comprises aggregating the RoDs scores for each variable and comparing the aggregate RoD score to a threshold. The threshold may be pre-determined or may be context dependent. In some aspects, a pre-determined threshold is based on the number of physiological variables measured for the patient. For instance, in embodiments in which an RoD is calculated for respiratory rate, heart rate, and blood pressure, there may be a pre-determined threshold of 3. As such, a high likelihood of deterioration in the future is determined when all three variables have an RoD score of 1, such that the RoDs for each variable are increasing. In other embodiments, more physiological variables are measured, and in such embodiments, the pre-determined threshold may be greater. Additionally, in some embodiments, the pre-determined threshold is not equal to the number of variables, but rather, the variables are used as a guide to determine the pre-determined threshold.

In some aspects, a tandem metric is also used in determining a likelihood of deterioration. In exemplary embodiments, the tandem metric is RMSSD. The RMSSD value may be used as a tandem metric to confirm the RoD scores, or, in an exemplary aspect, a change in RMSSD is used. For instance, an RoD score of "1" may be assigned to a physiological variable only when there is an increase in both the RoD and the RMSSD for that variable. This tandem metric, such as RMSSD, acts as a confirmatory metric to reduce the risk of false positives and false negatives. It is also contemplated that other metrics may be used for the tandem metric, such as standard deviation.

At step 270, a response action based on the likelihood determined at step 260 is initiated. The response action being initiated may be based on the aggregate RoD score exceeding the threshold. One such response action may be a notification that is emitted or otherwise communication to a caregiver responsible for the patient's care. For instance, when the aggregate RoDs for the measured physiological variables satisfies the threshold, indicating a significant risk for deterioration exists, a notification of the determined risk, such as described previously, may be generated and communicated via a bedside alarm, user/clinician interface (such as interface 142 described in FIG. 1A), or may be communicated to a smartphone or personal computing device of a caregiver, thereby alerting them of an impending deterioration of the patient's condition. In one embodiment, the notification comprises an event signal and includes the likelihood of future deterioration. Additionally, some embodiments of step 270 may comprise storing the result of the determination in EHR associated with the patient and further may include providing the patient's EHR (or facilitating access to the EHR) in the notification.

In addition or alternative to the notification, a set of one or more actions relating to preventative and/or therapeutic responses may be initiated. For example, as described herein, a recommendation for modifying a care plan or treatment procedure associated with the patient may be provided based on the determined likelihood. For example, a recommendation may comprise increasing patient monitoring or level of care, operating on the patient, or administering a therapeutic intervention, such as a medication or procedure. The recommendation may be provided in conjunction with a notification of the likelihood of deteriorating condition, and/or may be provided via a user/clinician interface, such as interface 142, described in connection with FIG. 1A.

Yet another action that may be initiated based on the determined likelihood comprises automatically modifying computer code executed in a healthcare software program for treating the patient, thereby transforming the program at runtime. For example, in one embodiment, the modification comprises modifying (or generating new) computer instructions to be executed at runtime in the program, the modification may correspond to a change in a care plan, treatment procedure, or therapeutic intervention to be administered to the patient due to the determined likelihood of deterioration. In one instance, the modification comprises changing the executed computer instructions corresponding to monitoring the patient's condition, such as increasing the frequency of obtaining physiological measurements of the patient, or increasing sensitivity of monitoring physiological changes in a patient.

A further action that may be initiated based on the determined likelihood comprises scheduling healthcare resources for the patient. For example, in one embodiment, an operating room (OR) resource may be automatically reserved for the patient, OR staff may be notified and/or automatically scheduled, and transportation/support staff or resources for getting the patient to the OR may be called. In one embodiment, this action comprises modifying or updating a resource/scheduling electronic record in a resource/scheduling system, such as operated as part of a hospital system. In one embodiment, the action comprises, upon a sufficient determined likelihood of a deterioration, initiating a computer instruction that modifies the scheduling healthcare resources, which may include computer instructions for automatically alerting, scheduling, and/or notifying staff, reserving rooms, transportation, or other equipment/space, and which may include changing the priority of the patient (when compared to other patients) for receiving these resources. In some embodiments, the initiated actions may be based on the level of risk (i.e., the probability that the patient's condition will deteriorate within a future interval), and/or how impending the event is likely to occur (e.g. how far into the future time interval, which may provide a sense of urgency).

Figure 6A:
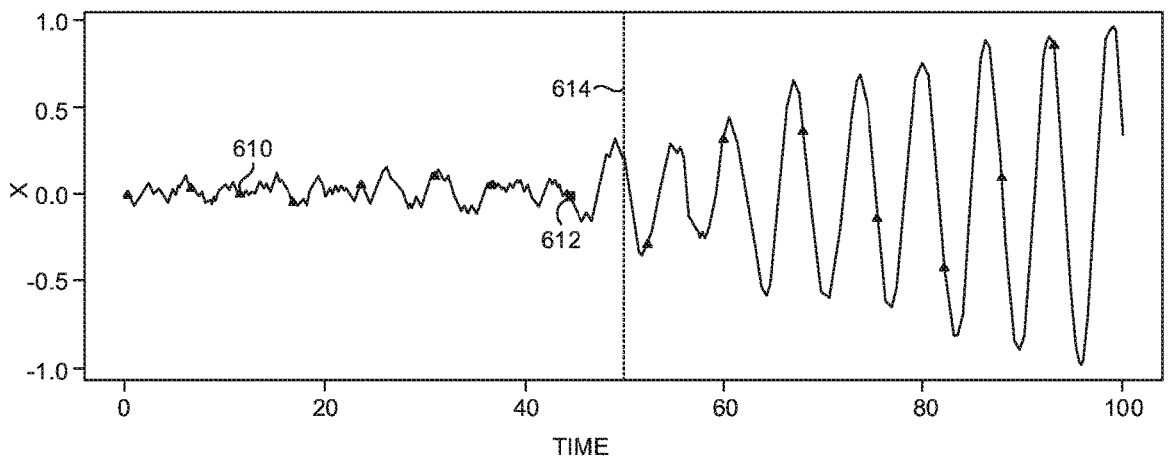
FIGS. 6A-6C depict graphical illustrations of an early warning detection system using ratio of deviations in accordance with an embodiment of the disclosure.
Figure 6B:
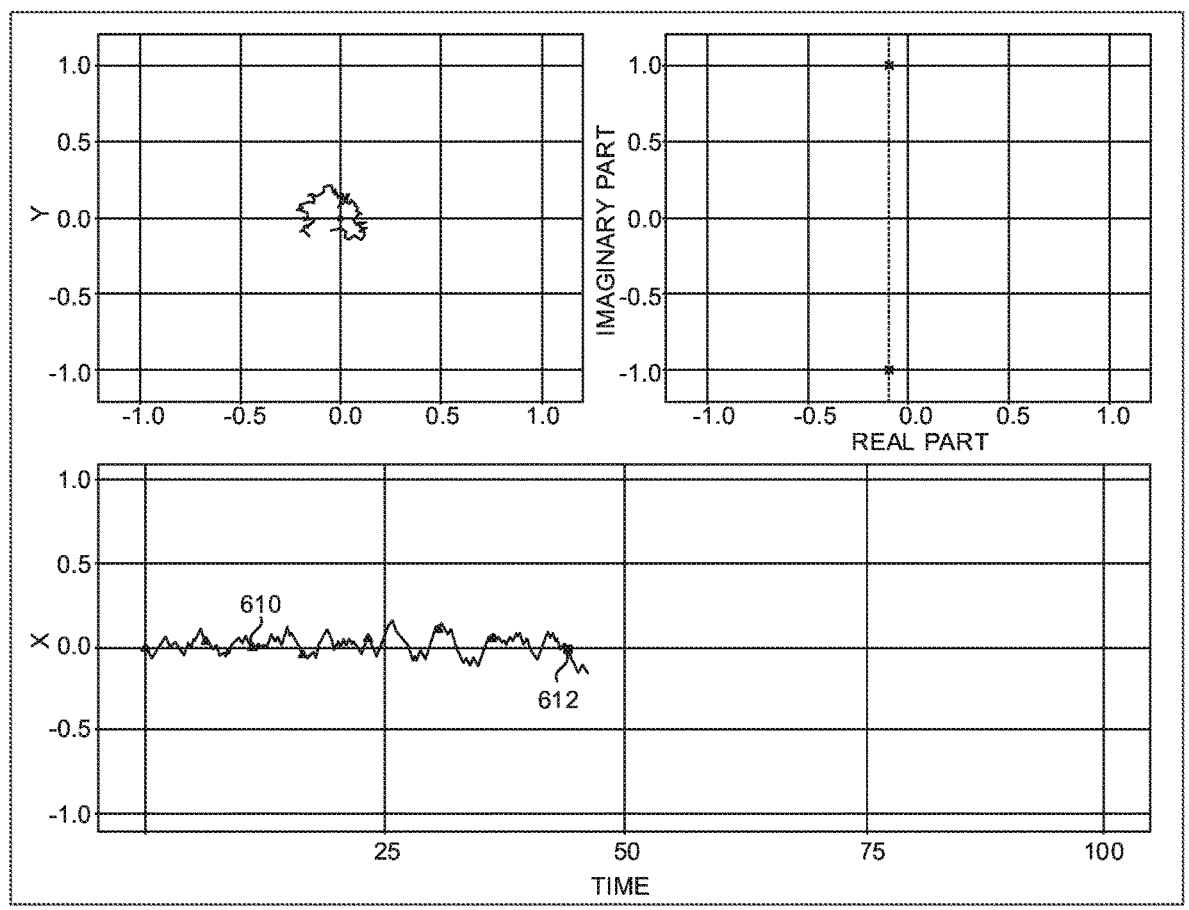
Figure 6C:
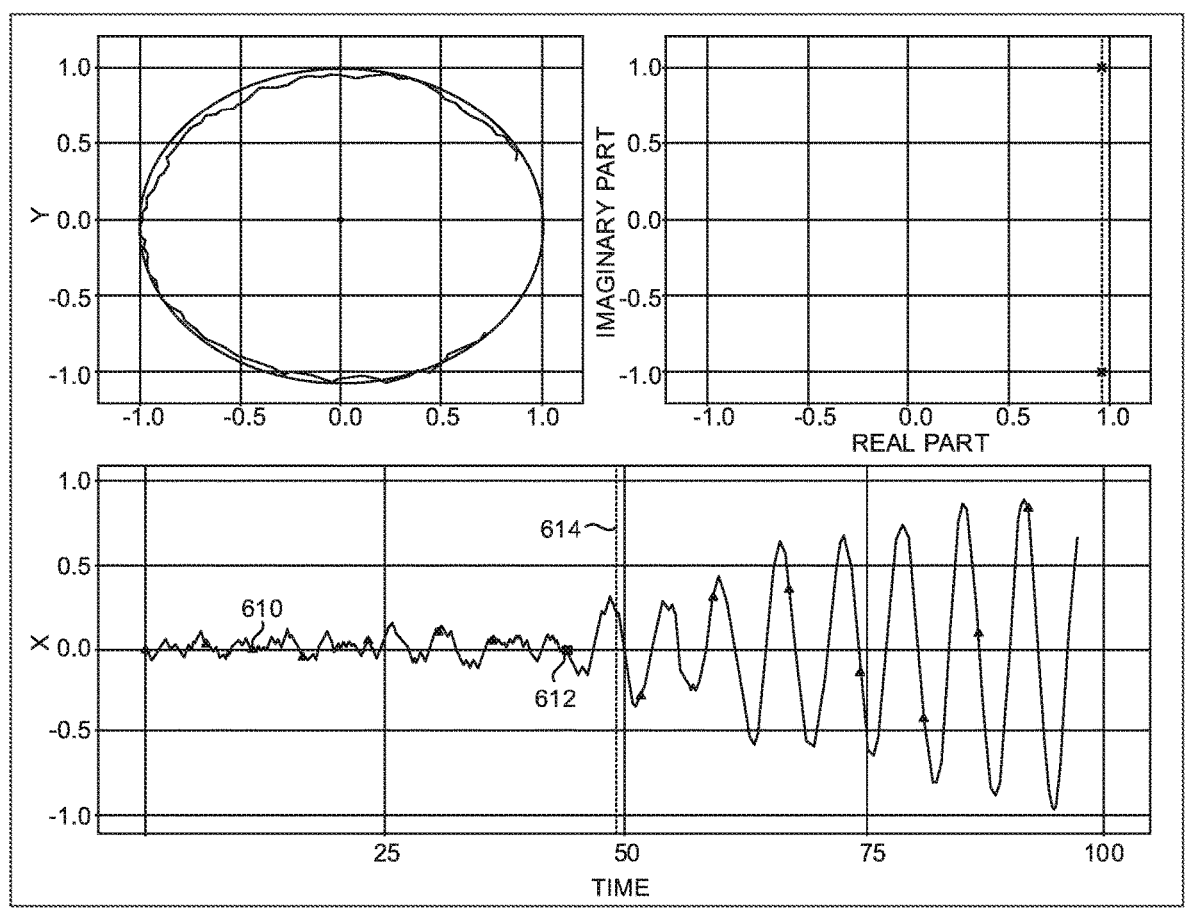

FIGS. 6A-6C depict an example of a time series 600 from which RoD is determined for use as an early warning signal, and further described below in the example reduction to practice. Observations 610, also referred to herein as measurements for a physiological variable, are being recorded over a time span. At observation 612, the RoD increases for both variables (x and y), which occurs at approximately t=45. Vertical line 614 represents the time at which the system undergoes dynamic Hopf bifurcation, which is at approximately t=50. Observation 612 represents a sample time series that randomly occur between four and eight time units after the previous observations. FIGS. 6B and 6C provide alternative views of the time series 600 at different points in time.

The time series 600 is based on an example of the Hopf normal form with additive white noise. The equations of the Hopf normal form are:

$$dx=[\lambda(t)x-y+2nx(x^2+y^2)-x(x^2+y^2)^2]dt+ndW_1$$

$$dy=[x+\lambda(t)y+2nx(x^2+y^2)-y(x^2+y^2)^2]dt+ndW_2 \qquad (8)$$

Additionally, n=0.25. The system was simulated from t=0 to t=100 using time steps of 0.05, and λ(t) was ramped linearly from −1 at t=0 to 1 at t=100, so the system underwent a dynamic Hopf bifurcation at (t, λ)=(50, 0). The time series for both x and y were sampled at times $t_i$, where $t_0$=0 and $t=t_i+$unif(4, 8) to generate sample time series $(x_i, y_i)$. The $x_i$ are depicted by triangles representing observations 610 and 612, for example, in FIGS. 6A-6C. Let $X_n=\{x_0, x_1, \ldots, x_n\}$ and define $Y_n$ similarly, and the RoD was computed for $X_n$ and $Y_n$ for each n. A change in the variable x was detected if both $RoD(X_{n+1})>RoD(X_n)$ and $\sigma(X_{n+1})>\sigma(X_n)$ (and similarly for y). Time series 600 in FIG. 6A is the time series for variable x, but a similar one may be constructed in graphical form for variable y.

Figure 7A:
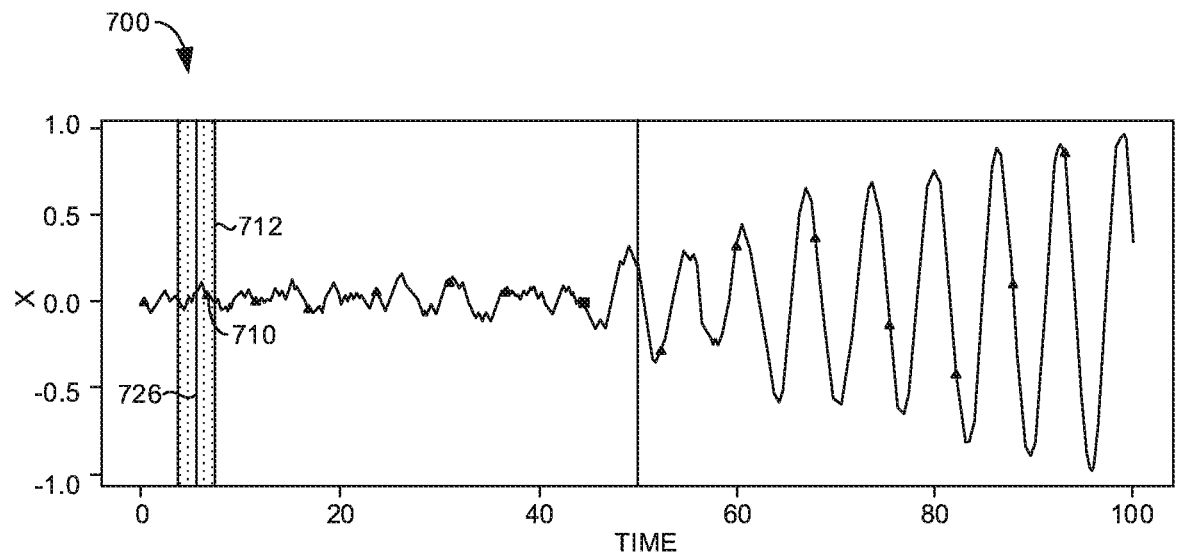
FIGS. 7A-7B depict various parameters of an early warning detection system using ratio of deviations in accordance with an embodiment of the disclosure.
Figure 7B:
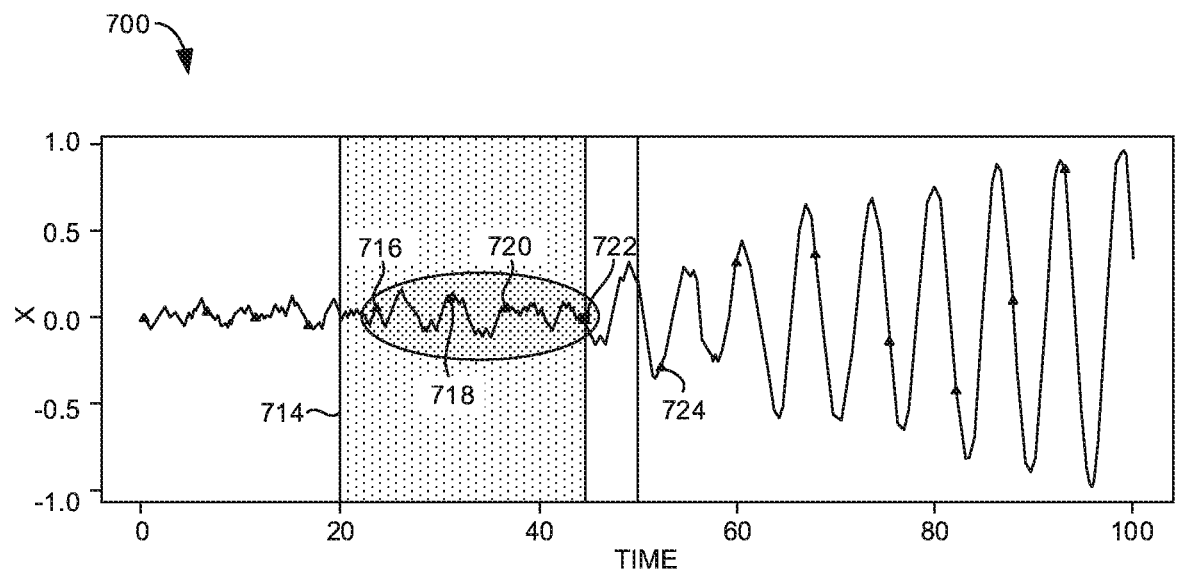

The RoD detection system described herein may operate in accordance with various tuning parameters, such as those illustrated in FIGS. 7A-7B. These tuning parameters may determine the frequency with which measurements are taken and the amount of measurements used for computation of each standard deviation and RMSSD. For example, as shown in FIG. 7A, one parameter may include a mean sample time, which refers to the mean time between observations. For instance, window 712 is the time in which an observation is being sampled from, and there is a mean sample time shown by vertical line 724 such that the next possible observation may occur after the end of the window 712. In some aspects, the mean sample time is approximately from two to eight hours.

Another tuning parameter may be window length. As referred to herein, window length indicates the period in the past in which observations are used for determining the RoD. Looking at FIG. 7B, if the current observation is observation 722 at t=45, window 714 shows the window length (or look back period) of 25 time units. With a window length of 25, there are four observations (716, 718, 720, and 722) that are used to compute the RoD at t=45. The RoD at t=55 would be determined back on a different set of four observations (718, 720, 722, and 724).

These tuning parameters—mean sample time and window length—may be pre-determined or set by a user as part of method 200 for detecting deterioration in a patient. These parameters may also be set to an optimal level based on other factors, such as the time units and the observation frequency. In some aspects, the optimal parameters are determined in a training process based on looking at the ROC curves, such as those provided in FIGS. 9A-9B, for time series based on different conditions. Observing systems in training may be useful to determine window length, noise-to-signal ratio, and mean sampling time.

EXAMPLE REDUCTION TO PRACTICE

With reference to FIGS. 8A-8E, 9A-9B, and 10A-10B and continuing reference to method 200 of FIG. 2, examples are provided of an embodiment of the disclosure constructively reduced to practice. Here, a computer system, such as computer system 120 running the operating system 129, was utilized with the open-source statistical software package R, and the 'deSolve' package in R. In this example embodiment, the performance of RoD as an early warning signal was tested on two different parameterizations of the Van der Pol system.

In certain parameter regimes, the Van der Pol system is an excitable system such that a small perturbation (in a particular direction) can lead to a big oscillation. Excitability is related to a separation of time scales and a phenomenon known as canard explosion. As used herein, canard explosion refers to a Hopf bifurcation in which the amplitude of the periodic orbits grows exponentially in terms of distance in parameter space from the bifurcation.

The variant of the Van der Pol system examined in the reduction to practice is provided below:

$$dx = \frac{1}{a}(3x - x^3 - y)dt + \sigma dW_1 \quad (9)$$
$$dy = [x - \lambda(t)]dt + \sigma dW_2$$
$$dz = (x - z)dt + \sigma dW_3$$

where a is a time scale parameter that affects the growth rate of the amplitude of periodic orbits. System (9) with a=10 is referred to herein as 'normal' because the amplitudes grow as expected according to a normal Hopf bifurcation. System (9) with a=1 is referred to herein as 'excitable' or 'with canard explosion' because the amplitudes grow much faster than normal.

In the reduction to practice, 200 simulations of each parameterization were run for each of five prescribed noise intensities ($\sigma$=0, 0.01, 0.05, 0.1, 0.25). In half of the runs, $\lambda$ was increased to pass through a Hopf bifurcation, and the other half of the simulations were control runs where $\lambda$ was held constant (i.e., $\lambda(t) \equiv \lambda_0$). The initial value $\lambda(0) = \lambda_0 = 1.2$ was chosen so that the system had an attracting equilibrium point, and the equilibrium point was used as the initial condition for the model. Each simulation ran for 2000 dimensionless time units with steps of 0.05 units. For the simulations in which $\lambda$ was increased, $d\lambda/dt$ was chosen so that $\lambda(1000) = \lambda_C = 1$ (i.e., $\lambda$ passed through the critical value exactly half-way through the simulation).

For high-frequency observations, RoD was not computed on the whole trajectory. Instead, the trajectories were observed iteratively at random times, so that $t_{i+1} = t_i + \Delta T$ where $t_0 = 0$, $\Delta T = \text{unif}(\alpha, \beta)$, and $\beta > \alpha > 0$. For each system, experiments varying ($\alpha$, $\beta$) were run, generating 100 time series from each trajectory for each of the values in Table 1 below. Additionally, the window length over which observations were used to calculate the RoD was varied, and windows of 250, 500, 750, and 1000 time units were used.

TABLE 1

Values used for experiments generating observations at random times.

| Experiment | $\alpha$ | $\beta$ | Mean Sampling Time = ($\alpha$ + $\beta$)/2 |
|---|---|---|---|
| 1 | 20 | 40 | 30 |
| 2 | 25 | 50 | 37.5 |
| 3 | 25 | 75 | 50 |
| 4 | 50 | 100 | 75 |

One goal was to detect bifurcations before they occur at t=1000, the window of 1000 time units representing an experiment using the entire trajectory. FIGS. 8A-8E illustrate the results of these experiments for each parameterization, noise intensities (sigma), window length, and observation rate when using RoD with RMSSD.

Figure 8A:
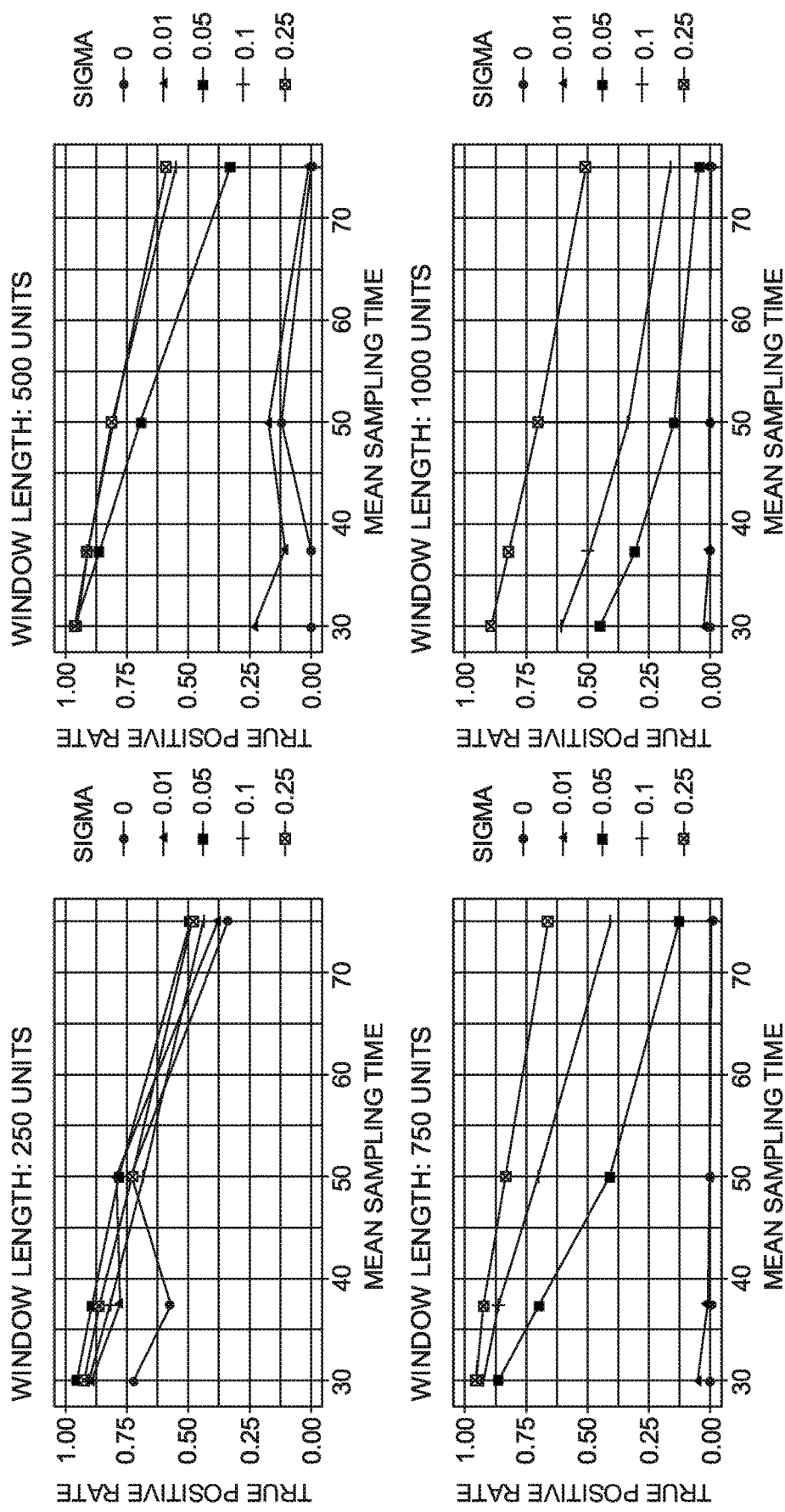
FIGS. 8A-8E depict graphical illustrations of the performance of an early warning detection system using ratio of deviations in embodiments reduced to practice.
Figure 8B:
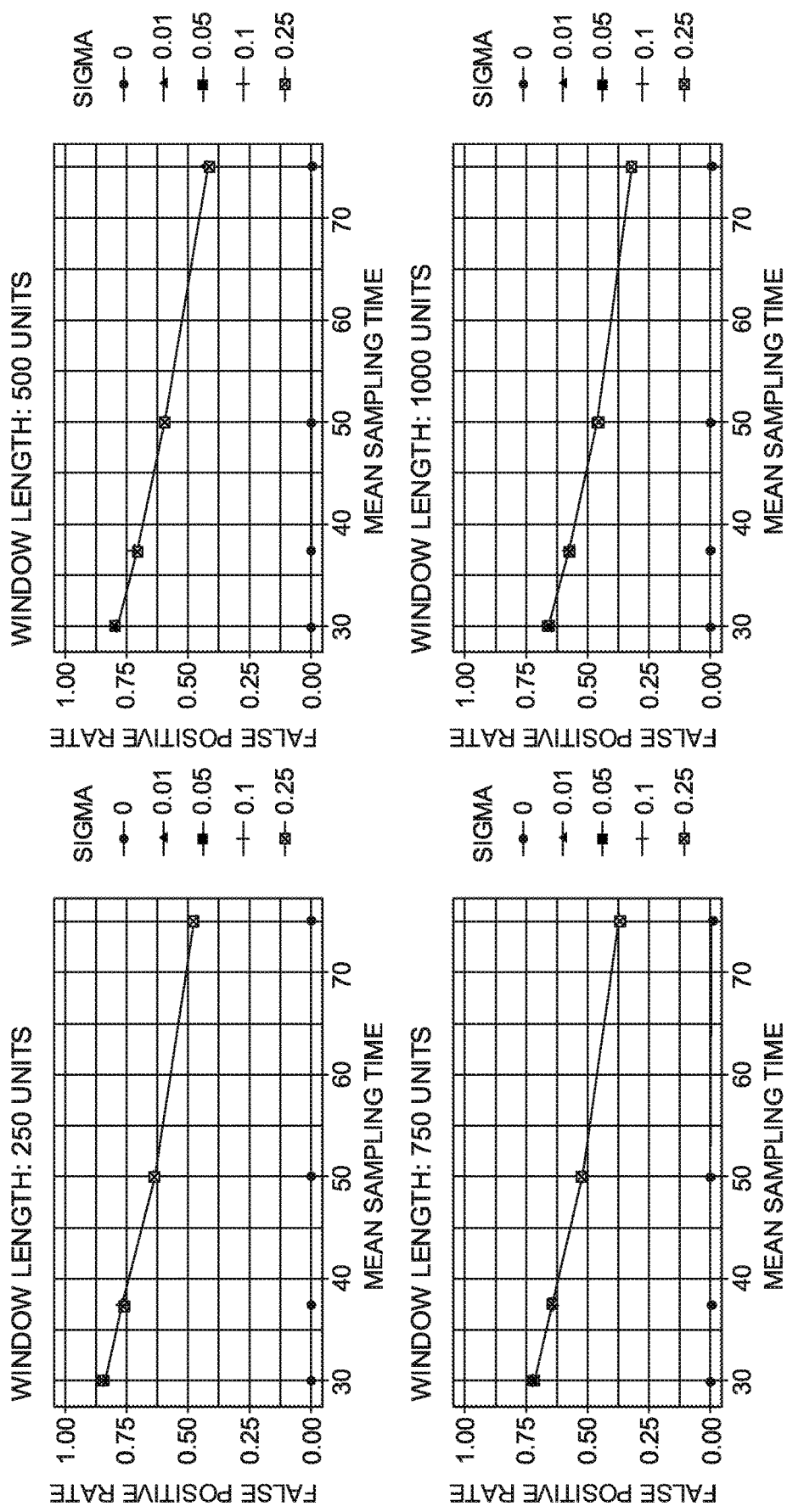
Figure 8C:
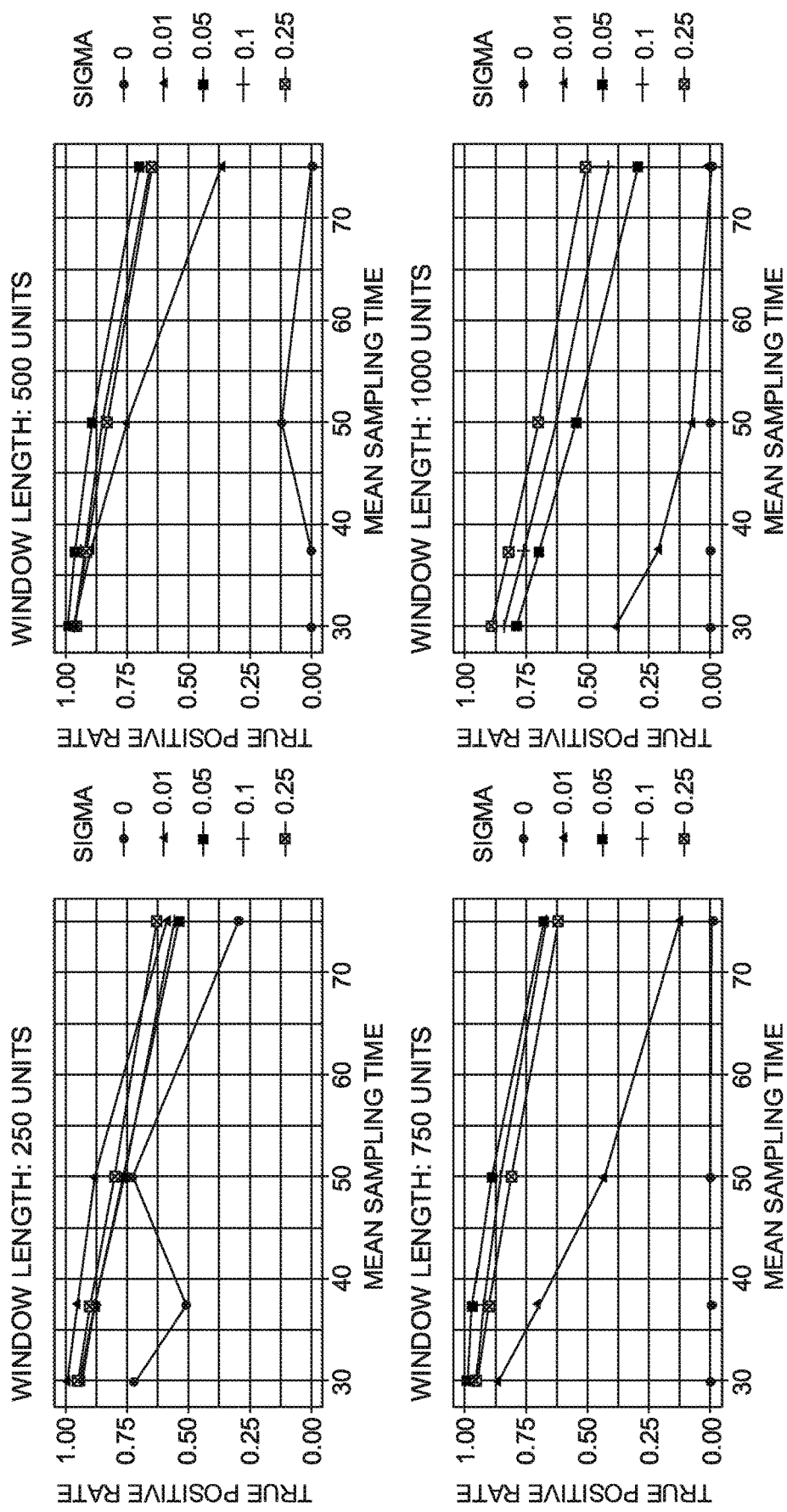
Figure 8D:
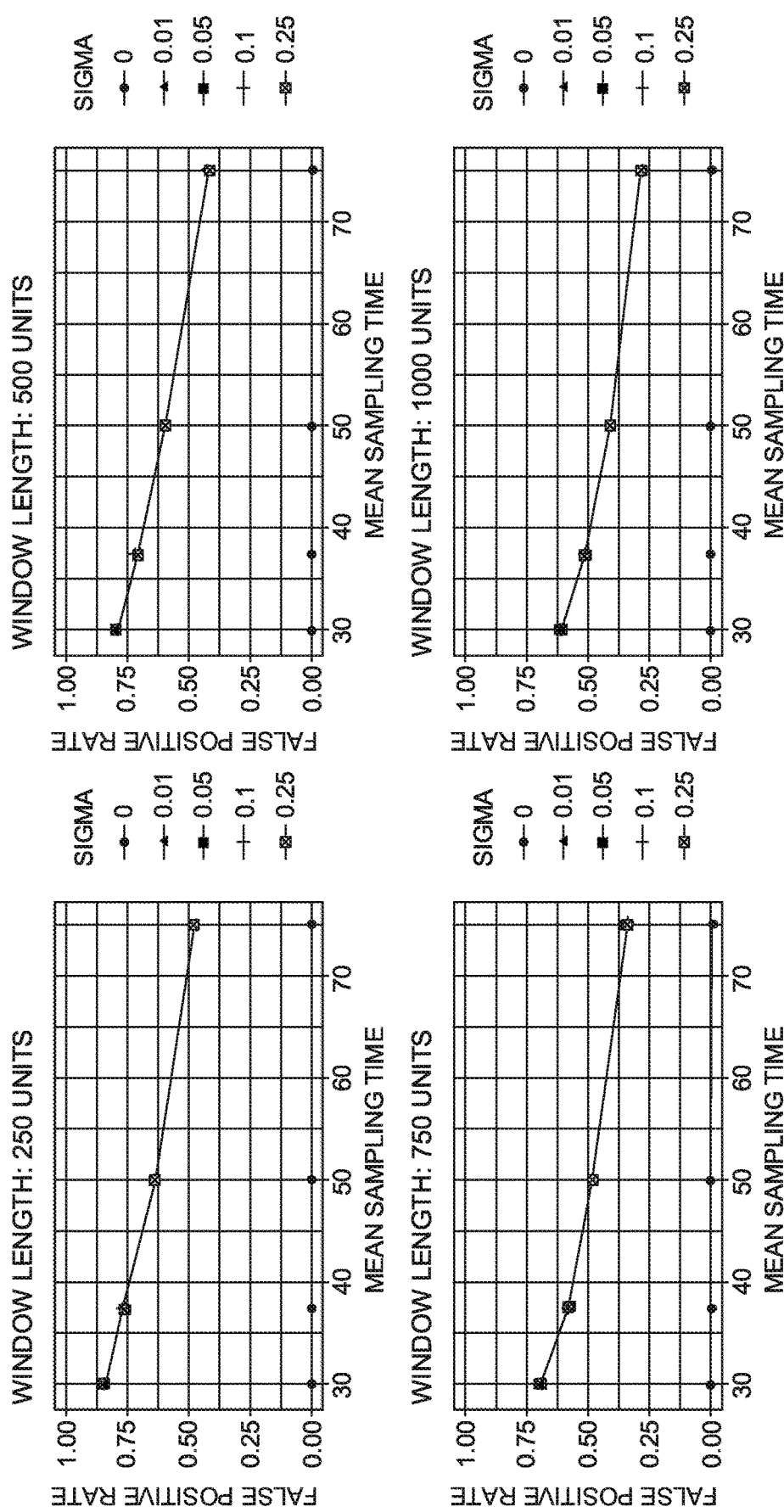
Figure 8E:
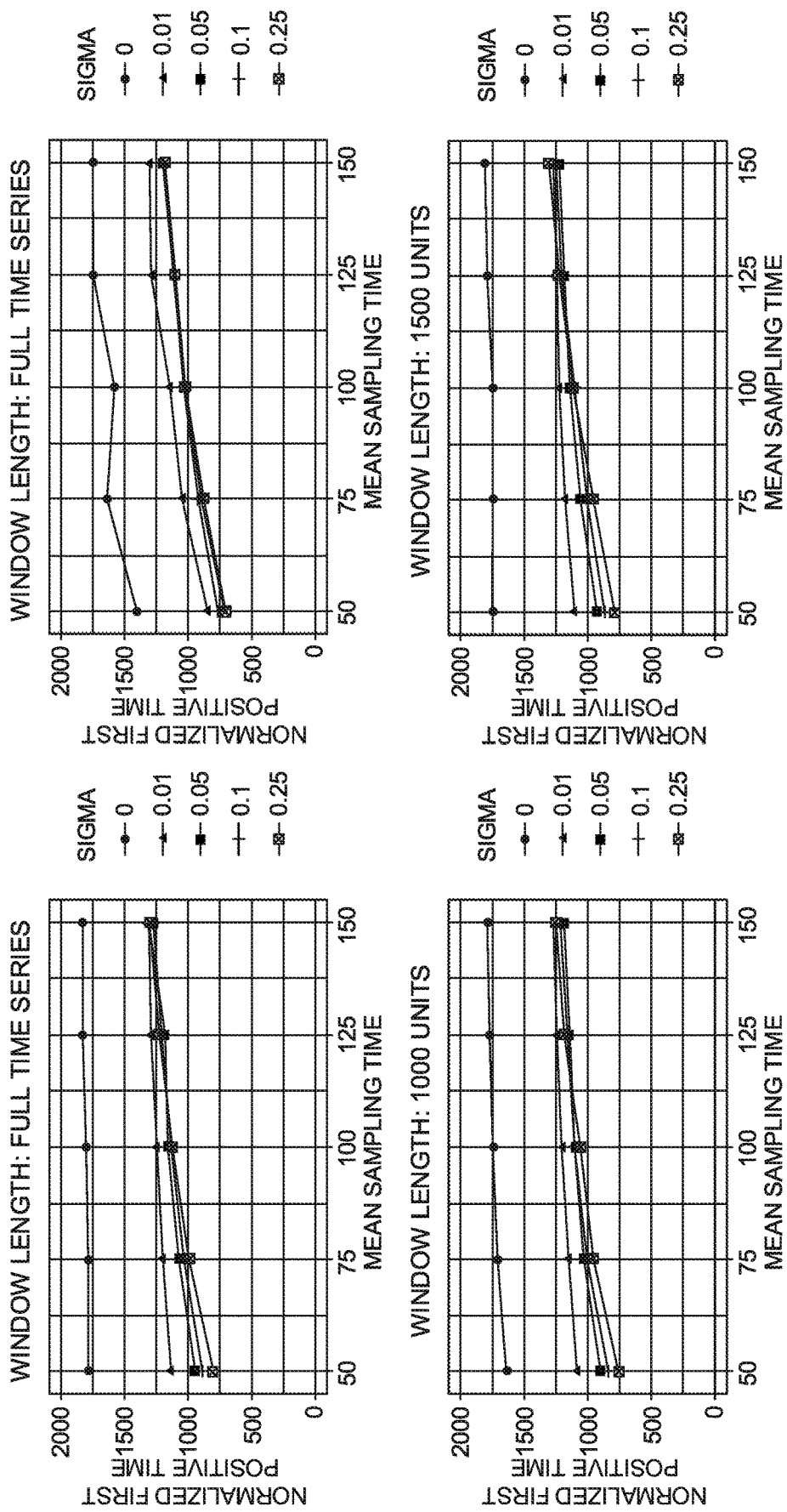

FIG. 8A depicts the rates of true positives on sampled time series in an excitable system, and FIG. 8B depicts the rates of false positives on the sampled time series in the excitable system. FIG. 8C depicts the rates of true positives on sample time series in a normal system, and FIG. 8D depicts the rates of false positives on the sampled time series in the normal system. Additionally, FIG. 8E illustrates the time to detection (as measured by the normalized first positive time) when using sparse observations. In this example reduced to practice, time to detection was approximately thirty minutes to twenty hours prior to the critical point, and the median time to detection was eight hours. As shown in these figures, noise may play a role in the performance of the detection system. The false positive rate may be affected by the presence of noise, but not the magnitude. Additionally, stronger noise may improve the true positive rate before bifurcation occurs.

The previously described reduction to practice dealt with low-frequency data (i.e., sparse observations). Embodiments have also been reduced with high-frequency data using the same trajectories as those simulated with low-frequency data. Even with high-frequency data, the data was sampled and RoD computed on random samples instead of using all of the observations in a given window. The same random samples of observations were used as with low-frequency simulations, but the samples utilized them differently. Previously, each sample of observations were treated as if it were the only data available to generate a binary prediction as to whether or not the system would undergo a Hopf bifurcation. With the high-frequency simulations, it was known that 100 predictions for each trajectory were generated, and they were used to determine a probability that the system would undergo a bifurcation.

Because a probability for each trajectory was being determined, performance could be measured using area under the curve (AUC) where 'the curve' refers to the receiver operating characteristic (ROC) curve. The ROC curve depicts the performance of a binary classifier as the threshold used to separate positive predictions from negative ones is varied. It was observed that a probability of 0.5 was not required to determine which trajectories were expected to undergo bifurcation. Accordingly, false positives from individual samples were no longer a concern, but rather, the concern was on trajectories as a whole, allowing RoD to be used alone as a test statistic (i.e., without RMSSD or SD as a tandem metric). It was found that RoD performed well as a classifier when using a window length of 500 (half of the full trajectory before bifurcation) with ($\alpha$, $\beta$)=(25, 75), yielding an average of 10 observations in each RoD calculation. FIGS. 9A and 9B depict the ROC curve for a normal system and an excitable system with ($\alpha$, $\beta$)=(25, 75) and a window length of 500. The AUCs with these parameters were 0.937 for the normal system and 0.98 for the excitable system.

In general, RoD performed well as a classifier in each of the experiments with between 8 and 14 observations expected to fall in each window. A window length of 500 with an average of 10 observations per window provided the best results, but the second-best performance also came with an average of 10 observations per window (and a window length of 750). Table 2 below lists the AUC for each of the experiments in which the expected number of observations per window was in the interval.

TABLE 2

Values used for experiments generating observations at random times.

| a | AUC | $\alpha$ | $\beta$ | Window | a | AUC |
|---|---|---|---|---|---|---|
| 1 | 0.867 | 25 | 50 | 500 | 10 | 0.830 |
| 1 | 0.980 | 25 | 75 | 500 | 10 | 0.937 |
| 1 | 0.876 | 50 | 100 | 750 | 10 | 0.911 |
| 1 | 0.840 | 50 | 100 | 1000 | 10 | 0.800 |

Many different arrangements of the various components depicted, as well as components not shown, are possible without departing from the spirit and scope of the present invention. Embodiments of the technology disclosed herein, for example, may be used for advance detection or early warning in systems having multiple variables that affect a dynamical system. For instance, RoD may be used to forecast events relating to bifurcation in dynamical systems, such as climate prediction, weather forecasting, chemical reaction networks, competition and population dynamics (e.g., predatory-prey systems), neural excitation, power grids (or similar electrical systems), seismology (or similar mechanical systems), and reaction-diffusion systems. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more non-transitory computer storage media having computer-executable instructions embodied thereon that when executed on a computerized decision support system, perform operations of a healthcare software program for anticipating deterioration in a patient, the operations comprising:
    electronically receiving a plurality of measurements of physiological variables for a patient, the plurality of measurements being acquired over a time span;
    constructing a time series from the plurality of measurements for each physiological variable measured;
    for each physiological variable, determining a plurality of standard deviations based on the time series;
    for each physiological variable, determining a plurality of root mean square of successive differences (RMSSD) based on the time series;
    for each physiological variable, forming a plurality of ratios of deviations (RoDs) for each set of standard deviation and RMSSD using the standard deviations and the RMSSDs, each RoD being a ratio of an RMSSD to a standard deviation;
    determining a likelihood of deterioration in the patient's condition within a future time interval based on detecting a Hopf bifurcation from the plurality of RoDs for the patient for each physiological variable; and
    automatically modifying operations of the healthcare software program including modifying a treatment plan, procedure or intervention for the patient based on the likelihood of deterioration, and modifying a frequency or sensitivity of measuring the physiological variables for the patient.

2. The media of claim 1, wherein the physiological variables comprise respiratory rate, heart rate, and blood pressure.

3. The media of claim 1, further comprising assigning an RoD score for each physiological variable based at least on an increase in the RoD for that physiological variable.

4. The media of claim 3, wherein determining a likelihood of deterioration in the patient's condition comprises:
    aggregating the RoD scores for each physiological variable to determine an aggregated RoD score for the patient; and
    comparing the aggregate RoD score to a threshold score.

5. The media of claim 4, wherein assigning an RoD score for each physiological variable is further based on a metric determined based on the time series for each physiological variable to confirm the RoD score, wherein the RoD score based on an increase in RoD for a physiological variable is confirmed when there is an increase in the metric.

6. The media of claim 5, wherein the metric is a change in RMSSD.

7. The media of claim 1, wherein the future time interval is within a range of thirty minutes to twenty hours.

8. The media of claim 1, wherein a set of measurements used to determine the standard deviation and the RMSSD is based on a window length, the window length being an amount of time units prior to a current measurement.

9. The media of claim 1, wherein each RoD is formed from a standard deviation determined from a set of measurements and an RMSSD determined from the set of measurements.

10. The media of claim 1, wherein the operations further comprise one or more of: automatically generating and communicating an electronic notification to a caregiver of the patient; generating and providing a recommendation for modifying a treatment procedure associated with the patient; or scheduling healthcare resources for the patient.

11. The media of claim 10, wherein the notification includes information indicating the determined likelihood of deterioration in the patient's condition within a future time interval.

12. A system for forecasting deterioration of a patient within a future time interval, the system comprising:
    one or more processors;
    computer storage media with computer-executable instructions that, when executed by the one or more processors on a computerized decision support system, perform a method of a healthcare software program for anticipating deterioration in a patient, the method comprising:
        electronically receiving a plurality of measurements of physiological variables for a patient, the plurality of measurements being acquired over a time span;
        constructing a time series from the plurality of measurements for each physiological variable measured;
        for each physiological variable, determining a plurality of standard deviations based on the time series;
        for each physiological variable, determining a plurality of root mean square successive of differences (RMSSD) based on the time series;
        for each physiological variable, forming a plurality of ratios of deviations (RoDs) for each set of standard deviation and RMSSD using the standard deviations and the RMSSDs, each RoD being a ratio of an RMSSD to a standard deviation;
        determining a likelihood of deterioration in the patient's condition within a future time interval based on detecting a Hopf bifurcation from the plurality of RoDs for the patient for each physiological variable; and
        automatically modifying operations of the healthcare software program including modifying a treatment plan, procedure or intervention for the patient based on the likelihood of deterioration, and modifying a frequency or sensitivity of measuring the physiological variables for the patient.

13. The system of claim 12, wherein the physiological variables comprise respiratory rate, heart rate, and blood pressure.

14. The system of claim 12, wherein determining a likelihood of deterioration in the patient's condition further comprises:
assigning an RoD score for each physiological variable based at least on an increase in RoD for that physiological variable;
aggregating the RoD scores for each physiological variable to determine an aggregated RoD score for the patient;
and comparing the aggregate RoD score to a threshold score.

15. The system of claim 12, wherein the system further comprises one or more sensors configured to automatically acquire the physiological data from the patient.

16. The system of claim 12, wherein a rate at which the measurements of the physiological variables are acquired from the patient is a non-uniform rate.

17. The system of claim 12, wherein the method further comprises one or more of: automatically generating and communicating an electronic notification to a healthcare provider responsible for the care of the patient; generating and providing a recommendation for modifying a care plan or treatment procedure associated with the patient; or scheduling healthcare resources for the patient.

18. A computerized method implementing a decision-support instrument for forecasting deterioration of a pediatric patient's condition, the method comprising:
electronically receiving a plurality of measurements of physiological variables for a patient, the plurality of measurements being acquired over a time span;
constructing a time series from the plurality of measurements for each physiological variable measured;
for each physiological variable, forming a first ratio of deviations (RoD) based on a first standard deviation and a first root mean square of successive differences (RMSSD) for the physiological variable using the time series, the first RoD being a ratio of an RMSSD to the first standard deviation;
for each physiological variable, forming a second RoD based on a second standard deviation and a second root mean square of successive differences for the physiological variable using the time series, the second RoD being a ratio of the second RMSSD to the second standard deviation;
determining a likelihood of deterioration in the patient's condition within a future time interval based on detecting a Hopf bifurcation from the first RoD and the second RoD for the patient; and
based on detecting the Hopf bifurcation, automatically modifying operations of the healthcare software program including modifying a treatment plan, procedure or intervention for the patient based on the likelihood of deterioration, and modifying a frequency or sensitivity of measuring the physiological variables for the patient.

19. The computerized method of claim 18, wherein determining the aggregated RoD score for the patient comprises adding the RoD scores for each physiological variable, the physiological variables comprising respiratory rate, heart rate, and blood pressure.

20. The computerized method of claim 19, wherein determining the likelihood of deterioration in the patient's condition comprises comparing the aggregate RoD score to a pre-determined threshold score, wherein the patient is determined to have a high likelihood of deterioration when the aggregate RoD score is three.

* * * * *

UNITED STATES PATENT AND TRADEMARK OFFICE
CERTIFICATE OF CORRECTION

| | |
|---|---|
| PATENT NO. | : 11,266,355 B2 |
| APPLICATION NO. | : 15/983348 |
| DATED | : March 8, 2022 |
| INVENTOR(S) | : Andrew Roberts, Sasanka Are and Douglas S. McNair |

It is certified that error appears in the above-identified patent and that said Letters Patent is hereby corrected as shown below:

In the Specification

Column 8, Line 34 delete "making" and insert -- making. --.

Column 14, Line 65 delete "px(1)" and insert -- $\rho$x(1) --.

Column 19, Line 65 delete "2nx(x2" and insert -- 2$\eta$x(x2 --.

Column 19, Line 65 delete "dt+ndW1" and insert -- dt+$\eta$dW1 --.

Column 19, Line 67 delete "2nx(x2" and insert -- 2$\eta$x(x2 --.

Column 19, Line 67 delete "dt+ndW2" and insert -- dt+$\eta$dW2 --.

Column 20, Line 1 delete "n=" and insert -- $\eta$= --.

In the Claims

Column 26, Line 19 in Claim 18, before "automatically" delete "based on detecting the Hopf bifurcation,".

Signed and Sealed this
Tenth Day of May, 2022

Katherine Kelly Vidal
*Director of the United States Patent and Trademark Office*